United States Patent
Boland et al.

(10) Patent No.: US 7,762,181 B2
(45) Date of Patent: Jul. 27, 2010

(54) CUSTOMISED NUTRITIONAL FOOD AND BEVERAGE DISPENSING SYSTEM

(75) Inventors: Michael John Boland, Palmerston North (NZ); Steven John Haylock, Palmerston North (NZ); Peter Aaron Munro, Palmerston North (NZ); David Lionel James Alexander, Ashhurst (NZ); Abby Kerrin Thompson, Palmerston North (NZ); Richard Archer, Palmerston North (NZ)

(73) Assignee: Fonterra Co-Operative Group Limited, Auckland (NZ)

( * ) Notice: Subject to any disclaimer, the term of this patent is extended or adjusted under 35 U.S.C. 154(b) by 1003 days.

(21) Appl. No.: 11/241,456

(22) Filed: Sep. 30, 2005

(65) Prior Publication Data

US 2006/0081653 A1    Apr. 20, 2006

Related U.S. Application Data

(60) Provisional application No. 60/615,444, filed on Oct. 1, 2004.

(51) Int. Cl.
*A47J 31/06* (2006.01)
(52) U.S. Cl. .......................................... 99/322; 99/321
(58) Field of Classification Search ........... 99/275–277, 99/483, 485–489, 467–476, 279–323, 325–333, 99/357; 141/168–172, 83; 705/2–6, 45, 705/231; 600/300; 708/132; 222/1, 8, 28, 222/52, 145.5, 146.2, 144.5
See application file for complete search history.

(56) References Cited

U.S. PATENT DOCUMENTS

| | | | |
|---|---|---|---|
| 3,534,676 | A | 10/1970 | Rubino |
| 3,702,583 | A | 11/1972 | Rullman |
| 3,871,156 | A | 3/1975 | Koeng et al. |
| 4,030,632 | A | 6/1977 | Harashima |
| 4,438,683 | A | 3/1984 | Bartfield |
| 4,514,094 | A | 4/1985 | Buckholz |
| 4,847,764 | A | 7/1989 | Halvorson |

(Continued)

FOREIGN PATENT DOCUMENTS

CA    2362898 A    6/2002

(Continued)

OTHER PUBLICATIONS

Kao et al., "A Dietary Recommendation in Expert System Using OPS5" 1987, Proc. 1987 Fall Joint Complete Conference IEEE Comput. Soc., pp. 658-663.

*Primary Examiner*—Thor S Campbell
*Assistant Examiner*—Vinod D Patel
(74) *Attorney, Agent, or Firm*—Knobbe Martens Olson & Bear LLP

(57) ABSTRACT

A system for dispensing a customized nutritional serving is made up of ingredients stored within a device incorporating the system. The device has a controller in whose memory is stored an inventory of the ingredients available in the device, their compositions and properties and customer profile data. The controller is programmed to formulate a serving which best matches the customized serving selected by the customer within constraints set by the programming taking into account the inventory of ingredients and the health profile of the customer. The customer is then presented with the selected serving and either accepts it or modifies it. The device is then programmed to prepare and dispense the final selection.

26 Claims, 14 Drawing Sheets

U.S. PATENT DOCUMENTS

| | | | |
|---|---|---|---|
| 4,919,950 A | 4/1990 | Mak | |
| 4,951,197 A | 8/1990 | Mellinger | |
| 5,113,753 A | 5/1992 | Robinson | |
| 5,163,356 A | 11/1992 | Chigira | |
| 5,197,376 A | 3/1993 | Bird et al. | |
| 5,233,520 A | 8/1993 | Kretsch et al. | |
| 5,237,910 A | 8/1993 | Chigira | |
| 5,299,529 A | 4/1994 | Ramirez | |
| 5,309,824 A | 5/1994 | Dromgoole | |
| 5,365,835 A | 11/1994 | Naramura | |
| 5,390,238 A | 2/1995 | Kirk et al. | |
| 5,392,209 A * | 2/1995 | Eason et al. | 707/3 |
| 5,412,564 A | 5/1995 | Ecer | |
| 5,542,420 A | 8/1996 | Goldman | |
| 5,596,994 A * | 1/1997 | Bro | 600/545 |
| 5,642,485 A | 6/1997 | Deaton | |
| 5,649,114 A | 7/1997 | Deaton | |
| 5,672,154 A | 9/1997 | Sillen et al. | |
| 5,673,691 A | 10/1997 | Abrams | |
| 5,687,322 A | 11/1997 | Deaton | |
| 5,704,350 A * | 1/1998 | Williams, III | 600/300 |
| 5,713,485 A | 2/1998 | Liff | |
| 5,722,418 A * | 3/1998 | Bro | 600/545 |
| 5,797,515 A | 8/1998 | Liff | |
| 5,823,392 A | 10/1998 | Madico | |
| 5,842,179 A * | 11/1998 | Beavers et al. | 705/28 |
| 5,881,632 A | 3/1999 | Fadoul | |
| 5,954,640 A * | 9/1999 | Szabo | 600/300 |
| 5,985,559 A | 11/1999 | Brown | |
| 5,997,924 A | 12/1999 | Olander | |
| 6,000,828 A | 12/1999 | Leet | |
| 6,024,013 A | 2/2000 | Goharrizi | |
| 6,024,281 A | 2/2000 | Shepley | |
| 6,038,546 A | 3/2000 | Ferro | |
| 6,039,688 A | 3/2000 | Douglas et al. | |
| 6,068,156 A | 5/2000 | Liff | |
| 6,112,645 A | 9/2000 | Chang | |
| 6,188,988 B1 | 2/2001 | Barry | |
| 6,283,322 B1 | 9/2001 | Liff | |
| 6,283,914 B1 | 9/2001 | Mansfield et al. | |
| 6,304,797 B1 | 10/2001 | Shusterman | |
| 6,321,641 B1 | 11/2001 | Wang | |
| 6,334,108 B1 | 12/2001 | Deaton | |
| 6,363,837 B1 | 4/2002 | Sham | |
| 6,377,935 B1 | 4/2002 | Deaton | |
| 6,383,542 B1 | 5/2002 | Khodor | |
| 6,424,949 B1 | 7/2002 | Deaton | |
| 6,471,089 B2 | 10/2002 | Liff | |
| 6,474,501 B1 | 11/2002 | Volpatti | |
| 6,510,430 B1 | 1/2003 | Oberwager | |
| 6,598,514 B2 | 7/2003 | Leggi | |
| 6,647,864 B1 | 11/2003 | Fang | |
| 6,672,341 B2 | 1/2004 | Bartholomew | |
| 6,684,195 B1 | 1/2004 | Deaton | |
| 6,776,304 B2 | 8/2004 | Bossi | |
| 6,814,254 B2 | 11/2004 | Liff | |
| 6,814,255 B2 | 11/2004 | Liff | |
| 6,829,431 B1 * | 12/2004 | Haven et al. | 392/441 |
| 6,843,166 B1 | 1/2005 | Li | |
| 6,871,676 B2 | 3/2005 | Sus | |
| 6,899,018 B2 | 5/2005 | Narcissi | |
| 6,953,342 B2 | 10/2005 | Bisogno | |
| 6,980,999 B1 | 12/2005 | Grana | |
| 7,090,638 B2 | 8/2006 | Vidgen | |
| 7,295,889 B2 * | 11/2007 | Lahteenmaki | 700/233 |
| 2001/0034023 A1 | 10/2001 | Stanton | |
| 2002/0004749 A1 | 1/2002 | Froseth et al. | |
| 2002/0082869 A1 | 6/2002 | Anderson | |
| 2002/0091596 A1 | 7/2002 | Dudek | |
| 2002/0113077 A1 | 8/2002 | Topliffe et al. | |
| 2002/0114834 A1 | 8/2002 | Her | |
| 2002/0138201 A1 | 9/2002 | Greensides | |
| 2002/0179639 A1 | 12/2002 | Bartholomew | |
| 2003/0010791 A1 | 1/2003 | Gentiluomo | |
| 2003/0149635 A1 | 8/2003 | Burklow | |
| 2003/0158624 A1 | 8/2003 | Kimura | |
| 2003/0158756 A1 | 8/2003 | Abramson | |
| 2003/0182160 A1 | 9/2003 | Lahteenmaki | |
| 2003/0189058 A1 | 10/2003 | Liff | |
| 2004/0238555 A1 | 12/2004 | Parks | |
| 2005/0048461 A1 | 3/2005 | Lahteenmaki | |
| 2005/0160005 A1 | 7/2005 | Roth | |
| 2005/0177397 A1 | 8/2005 | Kane | |
| 2005/0199646 A1 | 9/2005 | Moy | |
| 2005/0210834 A1 | 9/2005 | Kamineni | |
| 2005/0211768 A1 | 9/2005 | Stillman | |
| 2005/0240444 A1 | 10/2005 | Wooten et al. | |
| 2006/0074279 A1 | 4/2006 | Brover | |
| 2006/0099310 A1 | 5/2006 | Koekkoek | |

FOREIGN PATENT DOCUMENTS

| | | |
|---|---|---|
| EP | 0409231 A1 | 7/1990 |
| EP | 0427875 A1 | 5/1991 |
| EP | 0896222 A2 | 2/1999 |
| EP | 1176539 A1 | 10/2002 |
| EP | 1382321 A1 | 10/2004 |
| JP | 07271857 | 10/1995 |
| JP | 2002-024402 | 1/2002 |
| JP | 2002-245536 | 8/2002 |
| JP | 2003-050654 | 2/2003 |
| JP | 2003-141337 | 5/2003 |
| JP | 2004086660 A | 3/2004 |
| WO | WO 91/00021 | 1/1991 |
| WO | WO 93/07085 | 4/1993 |
| WO | WO 95/02387 | 1/1995 |
| WO | WO 95/25423 A2 | 9/1995 |
| WO | WO 99/32065 | 7/1999 |
| WO | WO 99/41575 | 8/1999 |
| WO | WO 99/66459 | 12/1999 |
| WO | WO 00/51053 | 8/2000 |
| WO | WO 00/51057 | 8/2000 |
| WO | WO 00/78163 A2 | 12/2000 |
| WO | WO 01/11980 A2 | 2/2001 |
| WO | WO 01/12036 A2 | 2/2001 |
| WO | WO 01/12039 A2 | 2/2001 |
| WO | WO 01/46016 A1 | 6/2001 |
| WO | WO 01/59669 A2 | 8/2001 |
| WO | WO 01/68534 A1 | 9/2001 |
| WO | WO 01/69487 A2 | 9/2001 |
| WO | WO 01/95230 | 12/2001 |
| WO | WO 01/97633 A2 | 12/2001 |
| WO | WO 02/12112 A2 | 2/2002 |
| WO | WO 02/25608 A1 | 3/2002 |
| WO | WO 02/37398 A2 | 5/2002 |
| WO | WO 02/081015 A1 | 10/2002 |
| WO | WO 03/005295 A1 | 1/2003 |
| WO | WO 03/020598 A2 | 3/2003 |
| WO | WO 03/026458 A2 | 4/2003 |
| WO | WO 03/056492 | 7/2003 |
| WO | WO 03/056492 A1 | 7/2003 |
| WO | WO 03/056493 | 7/2003 |
| WO | WO 03/056493 A1 | 7/2003 |
| WO | WO 03/089301 A1 | 10/2003 |
| WO | WO 03/101225 | 12/2003 |
| WO | WO 03/101255 A3 | 12/2003 |
| WO | WO 2004/010799 A2 | 2/2004 |
| WO | WO 2004/036515 A1 | 4/2004 |
| WO | WO 2004/084647 | 10/2004 |
| WO | WO 2004/084647 A2 | 10/2004 |
| WO | WO 2004084647 A2 | 10/2004 |
| WO | WO 2005/027716 A2 | 3/2005 |
| WO | WO 2005/053608 A2 | 6/2005 |

* cited by examiner

CUSTOMISED NUTRITIONAL FOOD AND BEVERAGE DISPENSING SYSTEM

CROSS-REFERENCE TO RELATED APPLICATIONS

The present application claims priority to U.S. Provisional Application No. 60/615,444, filed Oct. 1, 2004, the disclosure of which is incorporated by reference herein.

BACKGROUND OF THE INVENTION

1. Field of the Invention

This invention relates to an automated food and beverage delivery system. More particularly it relates to an automated food and beverage delivery system which provides customized servings based on customer choice and stored customer profile, health and nutritional data.

2. Description of the Related Art

Vending machines which sell pre-packaged foods and beverages are known in the art. Vending machines are also known which dispense beverages such as coffee, hot chocolate or soft drinks where the customer selects the combinations and the machine dispenses each of the components from storage containers in measured amounts into a single receptacle which the customer removes from the machine.

In U.S. Pat. No. 5,404,796 there is described a vending machine which produces French fried potatoes from a dehydrated powder. The powder is rehydrated and the French fries formed in a die within the machine. The fries are then cooked in hot oil and dispensed freshly fried to the customer. The only capacity the device has for customisation is the choice of whether or not to dispense salt and/or a sauce.

Computer programs are known where the customer inputs a serving choice and the computer prepares a sample menu. This sample menu is based on possible combinations from ingredients available to the user. Japanese patent specifications JP 200305064 and JP 2003141337 are exemplary of such systems. It is then up to the customer to prepare a meal based on the menu prepared by the computer.

Described in WO 03/056493 is a nutrition dispenser for dispensing doses of nutrition and medicine which are customized to the needs of the customer. The customer inputs a request and the dose to be dispensed is formulated from the nutrients and medicines stored in the dispenser using rules based logic to compare the customer's health and nutritional needs with standard nutritional and medicine tables. The choices of the customer are limited by the rules governing the dispensing of ingredients by the dispenser.

It is an object of this invention to go some way to overcoming these disadvantages or at least to offer the public a useful choice.

SUMMARY OF THE INVENTION

The invention broadly consists in a system for dispensing a customized nutritional serving which comprises:
an ingredient storage module;
an ingredient processing module;
a serving dispenser;
a customer interface; and
a controller operatively linked to the customer interface and programmed to control the operation of the storage module, the processing module and the dispenser;
the controller having stored in its memory an inventory of ingredients in the storage module, their compositions and their properties, and customer profile data;
the controller being programmed to operate in the following manner:
when a customer selects a customized serving through the customer interface, the controller:
a) looks up the information stored in its memory, formulates a serving which best matches the customized serving selected by the customer within predetermined constraints set by its programming and presents a selected serving to the customer for confirmation or modification;
b) if the customer modifies the selection, repeats step a) on the modified selection, and presents the resulting selected serving to the customer for confirmation or modification; and
c) when the customer has confirmed a serving issues instructions to the ingredient storage and processing modules and the serving dispenser to prepare and dispense the serving.

In one embodiment the ingredient processing module and the serving dispenser are integral with one another.

In one embodiment the serving dispenser is at least partly operated by a customer or by an operator.

In one embodiment the predetermined constraints in the programming of the controller include but are not limited to one or more of the following:
limitations or physical properties of ingredients, compatibility of ingredients with one another, limitations on certain ingredients by health status, requirements of certain ingredients by health status, availability of ingredients in the inventory, and cost.

In one embodiment the controller is programmed so that as soon as a repeat customer has been identified through the customer interface, the customer is presented with a selected serving based on a previous selection of that customer, if the customer confirms the selection the controller skips directly to step c), if the customer selects a different serving the controller begins at step a).

In one embodiment in carrying out steps a) and b) the controller:
uses the customer profile data to generate nutritional requirements and targets for the customer and consults the inventory of ingredients to generate limits on the inclusion levels of each ingredient, and
selects ingredients to formulate a serving optimised to meet nutritional requirements within the constraints of available ingredients.

In another embodiment the controller selects ingredients to formulate a serving optimised to meet nutritional requirements within the constraints of other requirements.

In a further embodiment the other requirements include requirements that certain ingredients are not included together at incompatible levels and that the serving comprises sufficient but not excessive liquid ingredients in a way that departs as little as possible from nutritional targets, that matches as closely as possible the customer's preferred flavour choices, and that is as inexpensive as possible.

In an alternative, in the steps a) and b) the selected serving presented to the customer is determined through the use of a boolean-tree algorithm.

In one embodiment the ingredient storage module comprises a plurality of storage compartments.

In one embodiment some of the compartments contain powdered ingredients such as dairy powders or flour or other grain based food product.

In another embodiment some of the compartments contain stabilisers, hydrocolloids or emulsifiers.

In another embodiment some of the compartments contain condiments such as spices, herbs or salt.

In another embodiment some of the compartments contain nutrients such as vitamins, minerals or bioactives.

In another embodiment some of the compartments contain flavourings or flavour modifiers.

In another embodiment some of the compartments contain texturing ingredients.

In another embodiment some of the compartments contain liquids such as water, juice, milk or other potable liquids.

In another embodiment some of the compartments contain gels or emulsions.

In another embodiment some of the compartments contain dried fruit or vegetables, or fruit or vegetable extracts.

In another embodiment some of the compartments are chilled or frozen.

In another embodiment some of the compartments are heated.

In another embodiment the ingredients storage module contains a dosing means for dosing predetermined amounts of ingredients stored in compartments into a serving.

In another embodiment there is provided ingredient advancing means for moving ingredients from the ingredients storage module to the ingredient processing module.

The ingredient advancing means is one or more of mechanical, gravity, vacuum, air pressure, and liquid pressure.

In one embodiment the ingredient processing module contains one or more of a mixer, a heater, a cooler or a freezer.

In one embodiment the heater is a convection heater, microwave heater, pasteuriser, irradiator, ohmic heater or high frequency sound.

In one embodiment the serving dispenser is a nozzle.

In another embodiment, the serving dispenser is an extruder. The extruder may optionally be heated.

In another embodiment there is provided a means for dispensing containers or other receptacles to be in registry with the dispensing nozzle to receive servings from the serving dispenser.

In one embodiment the controller is operatively linked to one or more servers each having stored on its memory at least some of the inventory of ingredients in the storage module and possible servings available therefrom, nutritional and health data relating to ingredients in the storage module and possible servings therefrom, and at least some of the customer profile data.

In one embodiment the controller and/or server is operatively linked to an external database.

In another embodiment the external database contains information on health and nutrition.

In another embodiment the external database contains health information of a customer.

In another embodiment the external database is a health insurance database.

In one alternative the customer profile data includes health status, records of recent purchases and preferences.

In one alternative the customer interface is a touch panel or keyboard integral with the dispensing system.

In another alternative the customer interface is a cell phone operable from a location remote from the dispensing system.

In another alternative the customer interface is a customer computer operatively linked through to the internet to the system.

In a further alternative the customer interface is a card reader which reads information digitally or magnetically stored on a card presented by a customer.

In one alternative the controller is operatively linked to a billing function.

In one alternative the billing function is operatively linked to an electronic crediting/debiting system.

In another embodiment the billing function is actuable by the insertion of coins, banknotes, prepaid electronic cards or the like.

In another embodiment the invention is a network of systems as defined above operatively linked to one or more servers.

In another embodiment the invention consists in an apparatus for dispensing customized nutritional servings, which apparatus comprises the combination of components of the system and/or network herein above described.

"Serving" as used in this specification includes not only a ready to consume serving of a beverage or a food, but also concentrates, sauces, toppings, condiments, or premixes which a consumer can take away to add to or use to prepare other servings.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention also envisages constructions of which the following gives examples only.

BRIEF DESCRIPTION OF THE DRAWINGS

The invention may be more fully understood by having reference to the accompanying drawings, wherein.

DETAILED DESCRIPTION OF THE PREFERRED EMBODIMENTS

Figure 1:
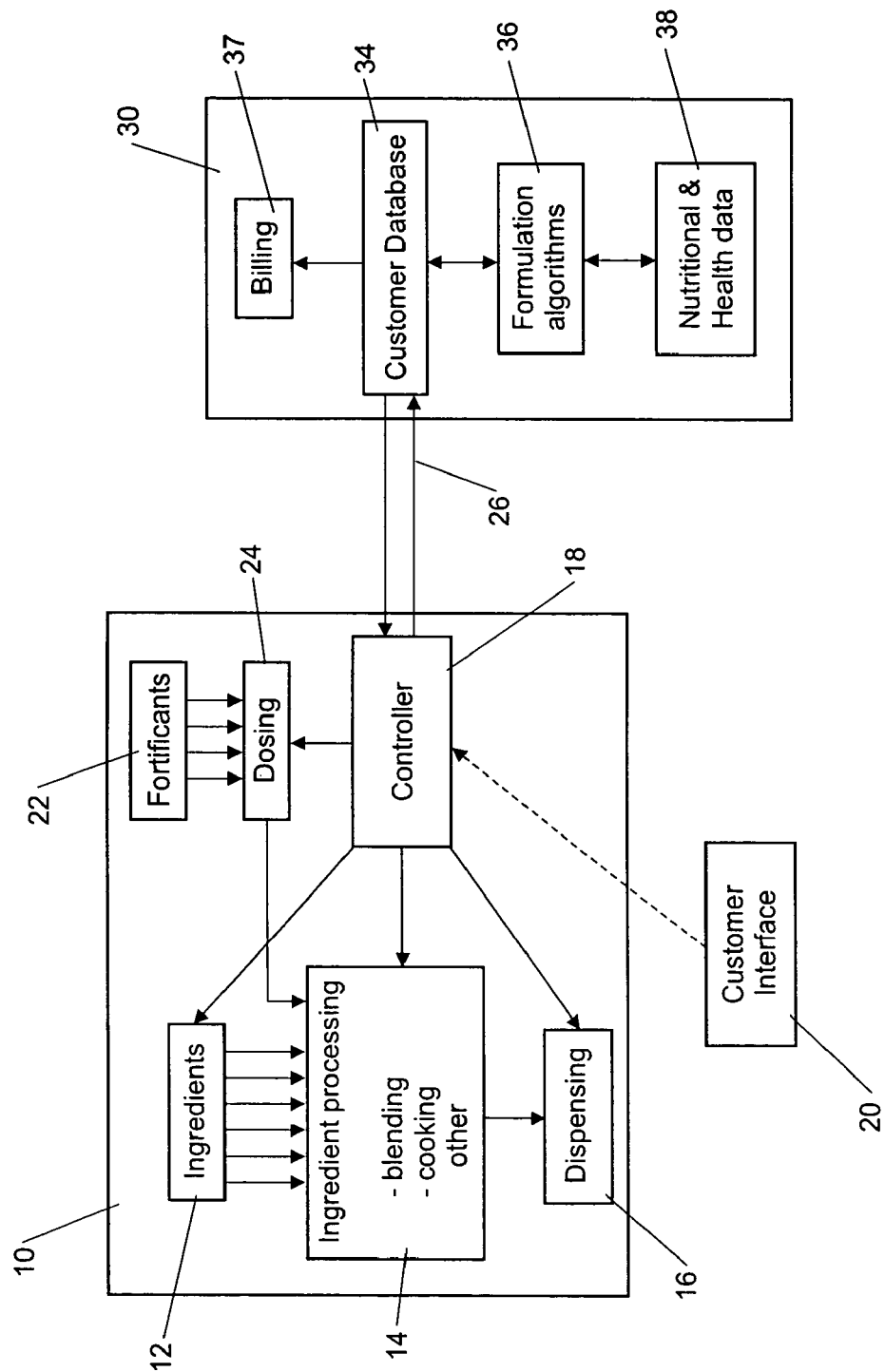
FIG. 1 is a block diagram showing the components of an embodiment of the invention.

The system according to the invention has both hardware components and software components. In the embodiment of FIG. 1 dispenser 10 is separate with from the server 30.

Dispenser 10 and server 30 are in electronic communication with each other. Although a server 30 may be integral with a dispenser 10, a single server 30 is usually linked with a network of dispensers 10.

The ingredients module 12 of the system will normally include a number of compartments containing bulk ingredients such as dairy powders or flour and other compartments containing ingredients designed to be dispensed in minute quantities such as condiments, nutrients, flavour modifiers and texturing ingredients. Typical dairy powders include whole milk powder, skim milk powder, milk protein concentrate and whey protein concentrate. The flour ingredients include grain and other vegetable flour. The flavour modifying ingredients include condiments such as spices, herbs or salt or other flavour modifying ingredient known to those skilled in the art. Artificial flavours or nature—identical flavours may also be included.

Some compartments may contain pre-prepared ingredient mixes to permit faster preparation times.

In an alternative embodiment the ingredient compartments may contain fresh, frozen or processed fruit, such as fruit pulp, for dispensing into beverages or other servings. In a system with such an embodiment the ingredients module may be equipped with the appropriate refrigeration.

The nutrients or other health promoting components to be included in storage compartments within the ingredients module are essential fats and fatty acids, vitamins, minerals and bioactives. Bioactives including freeze dried probiotics, bioactive hydrolysate powders and the like are also stored in the compartments.

Other components to be stored include but are not limited to: agar, alginates, arabic, carrageenan, carboxy methyl Cellulose (CMC), gelatine, konjac flour, locust bean gum (LBG), methyl cellulose and hydroxypropyl methyl cellulose (MC/HPMC), microcrystalline cellulose (MCC), pectin, xanthan, acacia gum, bacterial gums, tamarind, ghatti, karaya, glactomannon, gellan polysaccharides, inulin, amylase, amylopectin, exopolysaccharides, maltodextrin, gelatine, fibre, protein, transglutaminase or hydrolysate products, amino acids, antioxidants, sugars, ginseng, guarana or caffeine.

Some of the other components also have nutritional and other benefits. For example, inulin has benefits for diabetes and konjac flour reduces dysphagia among the elderly.

Bacterial cultures, particularly lactic acid bacterial cultures, may be included in a storage compartment for use in fermented drinks or yoghurt.

Compartments of the ingredients module 12 also contain processing liquids such as water, milk or other potable liquid.

Storage compartments also contain gels such as yoghurt or emulsions such as ice creams or the like.

Chilling or refrigerating means are provided for some storage compartments where the ingredients require such conditions.

Similarly where ingredients need to be kept at temperatures above ambient, heating means can be included.

The ingredient processing module 14 includes dosing mechanisms associated with the storage compartments. These are joined by conduits into the ingredient processing module. Means to advance ingredients along the conduits typically include gravity, fluid advancing means such as augers, air or liquid pressure, or vacuum pressure at the ingredient processing end of the conduits.

The ingredient processing module 14 includes mixing means in containers disposed to receive ingredients from the ingredients storage module 12. The mixing means include mixers commonly employed in the food industry for mixing dough ingredients or other mixers known in the art.

A forming mechanism is optionally provided for some functions of the system. The mixed ingredients are then passed to a forming mechanism for forming the combined ingredients into a predetermined shape such as a nutritional bar. This is forwarded to a heating means such as a convection oven/microwave oven, high pressure, ohmic heating or ultra high frequency sound.

In one embodiment if the food selected is a pizza, the forming mechanism is a roller. The pizza base is rolled out with the roller and at an intermediate station the pizza topping is sprinkled on the base from dosing mechanisms before it is cooked in a convention oven. Other flattening mechanisms may also be used.

Where the product to be dispensed is, for example, a fluid emulsion such as a yoghurt, it is dispensed out of a nozzle into a container. In one embodiment the dispensing module 16 has a nozzle which is accessible by the customer. The customer positions a container below the nozzle and allows the fluid serving to collect in the container.

In another embodiment the container and nozzle may not be accessible to the customer. The container may be filled and then sealed with an automatic sealing device before the sealed container is dispensed to the customer.

In another embodiment of the system the ingredient processing module and the serving dispenser are combined. This would be done, for example, where there are a limited number of powdered ingredients which are readily soluble in a liquid stream. The processing and dispensing functions would be dissolving the powder in the liquid and allowing the customer to take the beverage away.

Although the operation of the dispenser is fully automated in some embodiments, in others the processing or dispensing operations may include actions of a customer or an operator. The customer or operator may have to place a receptacle, such as a cup or pottle, under a dispenser and push a start button to dispense the serving. The customer or operator may have to assist in processing or dispensing ingredients by pushing buttons or levers as directed on a screen at the customer interface.

The dispenser may have associated with it a labelling unit. This unit will be able to print and attach a label which lists the ingredients and can give any special instructions required. The label can also include the nutritional properties provided by the serving.

The controller 18 is, in one embodiment, a microprocessor having a large number of functions. It will operate interactively with the storage module 12, with the ingredient processing module 14 and with the dispensing module 16 to ensure that the ingredients selected, dispensed and processed meet both the customer selection criteria and the health, nutritional and customer profile data requirements. It also will maintain a watch on the level of inventory and send signals to inventory operators when ingredient compartments need to be refilled.

The controller 18 will also interact with a billing module 32 in server 30. In some instances the dispenser will be coin, bank note or debit card operated in the manner of other vending machines. In other instances the billing will be done through conventional electronic direct debiting/crediting of the point of sale transaction.

The controller 18 will be able to access customer profile data 34. This may include previous customer menu selections and nutritional requirements of customers. Where the customer has a high level of fitness and has nutritional requirements for particular activities this will be accounted for in selecting the ingredients. Where a customer has allergies to certain foods (for example peanuts, gluten or phenylalanine) or has a condition, such as diabetes or high blood pressure, it will preclude the dispensing of ingredients which might aggravate the conditions.

The customer profile data 34 can, in its simplest form, contain basic information such as weight, height, age and current health status entered by the customer. Where the customer has had a more detailed health assessment or tests for certain conditions this information may be entered as well. For high performance sportspeople real time fitness information may be fed into the customer database and suitable nutritional beverages or other servings ordered for consumption at the end of or even during a workout.

When the customer has had a genotype analysis the resulting data may also be entered in the database. Nutrigenomics analyses enable the selection of servings best suited to the customer where a genotype analysis is available. Where a customer's purchases are paid for or subsidised by health insurance, making a claim at the time of purchase may be done through a linkage to the health insurance database.

The customer input will be though some form of customer interface 20. Where the system is already storing customer profile data, the customer will only need to enter a personal identification number (PIN). Other customer identification mechanisms such as iris scanning or electronic fingerprint recognition or recognition of other biometric data may be used as alternatives to PIN entry. Another alternative is the use of radio frequency identification (RFID) or transponder systems. The interface will include a screen or speaker so as to enable interaction between the controller and the customer.

The interface could be a cell phone, a computer with internet access, or it could be a keyboard or other input device on the machine itself activated by inserting a card which can be read electronically by the device. In one alternative the customer interface may be voice activated.

A customer may register on the system through the customer interface 20. Registration would normally include input of customer profile data. Where the customer has health information stored on an electronic card the transfer can be by the reading of that card. Alternatively, customers could key in information in response to standardised questions about preferences, health status and allergies. In another alternative health data of a customer stored on a remote computer may be accessed when authorised by the customer.

The memory would also have loaded on to it nutritional and health data 38 which can be compared with the customer's health profile to ensure that adverse ingredients are excluded. Alternatively, the controller can be programmed to access and interrogate databases such as the one at URL www.mypyramid.gov which provide health and nutritional recommendations.

The billing module 32 can be as simple as a connection to electronic crediting and debiting services offered by banks. Alternatively it can be a module taken from a conventional vending machine where coins, banknotes or electronic debit cards activate the device.

The dispenser 10 is also provided with a fortificant module 22, and a dosing unit 24 upstream of ingredient processing module 14. There is an electronic connection 26 between each dispenser 10 and server 30.

Server 30 has the following functions and memory databanks. The billing function 32 is described above. The customer database 34 contains customer profiles. In addition to individual profiles it can also generate customer group profiles to be referred to when processing orders from customers not previously registered. Server 30 will also have stored on it nutritional and health data 38 and formulation algorithms 36 for selecting ingredients to meet not only customer choice, but nutritional and health requirements.

A system in its simplest configuration would be a stand alone vending machine with all of the memory and programming functions within the controller.

Other embodiments consist of combinations of vending machines and a single server or multiple servers. Where there is a cluster of vending machines which is accessed by a regular set of customers, the customer profile data may be stored in the memories of each of the cluster of machines, or a local server to speed access and response times.

In operation a customer will enter their PIN or other identifier and select a serving. In a typical embodiment the customer will be presented with a menu starting with meal and snack types from which menu choices may be made.

The formulation of the menu types can either be through a general selection offered to all customers or, where the customer profile data restricts the food type, from a more restricted menu.

The customer makes his/her selection and the controller 18 will then actuate the switches governing the dispensing of ingredients leading to the mixing of the ingredients and cooking of the ingredients, where required, and then dispensing them from the machine. The size of the portions will be determined by reference to the customer profile data 34.

In one embodiment the customer is present at the dispenser 10 and waits to collect the serving when it has been dispensed. In more sophisticated models where the customer has ordered a serving from a site remote from the machine (by cell phone or via the internet) the customer will enter input data to allow release of the serving from a dispensing station in the machine itself. Such a facility would be important where there is a time delay between the time when the meal or snack has been ordered and it is dispensed by the machine.

The system and apparatus according to the invention will also optionally contain a hygiene management system. Such a system would monitor accidental spillages and the like. When a spillage was detected the machine in question would be disabled until the spillage had been cleaned by an operator.

Where an ingredient has a limited shelf life, this information is part of the ingredient control database data. When the ingredient is placed into a compartment of the ingredients module the date is noted and the ingredient dosing mechanism disabled once the "use by" date has passed until fresh ingredient is added.

Although not intended to be limiting, typically machines incorporating the system of the invention will provide servings of a particular type. Some machines will dispense drinks such as "smoothies" or drinking yoghurts. Other machines will dispense nutritional bars mixed and formed according to the customer choice. Other machines will serve soft food such as mousses, yoghurts or ice creams. Still other machines will provide topping products such as cheese melts and pizzas.

In another embodiment the serving dispensed may be a concentrate, powder, sauce, topping or the like which is taken away and used to prepare a beverage or mix with or sprinkle on other foods such as salads, meat, vegetables, fish or the like.

Access to machines may be by membership or casually. Customers who are members will be able to have their servings customized according to their preferences and limitations in their profile data.

Machines incorporating systems according to the invention can be installed in schools. Such machines may not have individual customer data but will have profiles of typical school age children. They will be programmed to produce smaller servings with nutritional compensation for potentially deficient diets and other meals. For example, adolescent girls would receive extra calcium in their servings. The ingredients stored in such machines would be limited to the range to meet the nutritional requirements of the schools.

In another embodiment a machine incorporating a system according to the invention would be programmed to deliver servings suited for consumption by elderly persons. Such machines would hold the customer profile data for each of the residents of a rest home. Meals would then provide for the nutrition and health requirements of each of the individual residents. The meal requests could be made by the residents themselves or by staff on their behalf. The installation of such machines could reduce the requirement for providing kitchens and kitchen staff in rest homes. The ingredients stored in such machines would also be limited to meet the needs of the elderly persons.

The programming of machines may include information about typical tastes of target groups as well as preferred textures of food.

Another potential use of vending machines incorporating a system according to the invention is in public transport. Buses, trains or airplanes; or airports or stations could be provided with such machines to dispense either customized or casual servings to travellers.

Vending machines incorporating the system of the invention can be located in retail chain stores, in shopping malls, supermarkets, convenience stores, universities, gymnasiums, workplaces, stadiums, theatres or any other place where potential customers are likely to be seeking food or beverages.

In one use a vending machine according to the invention is installed adjacent to the sales counter of a convenience food outlet. The customer takes a purchased food item, such as a salad, to the vending machine and orders a serving, such as a dressing, which may either be dispensed directly onto the salad, or in a packet which the customer opens before spreading the dressing onto the salad.

The system according to the invention offers several advantages. In one embodiment the customer is offered the convenience of a serving which is not only customized according to preference, but also optimised for health and nutrition considerations too. Where the serving is prepared from fresh ingredients, these may be stored in conditions where they are presented in a serving in a fresher state than if they had been stored in less optimum conditions by the customer. The algorithm controlling the storage and dispensing of ingredients can be programmed to ensure that freshness is a consideration which is included.

Vending Machine With Nutritional Beverage

Figure 2:
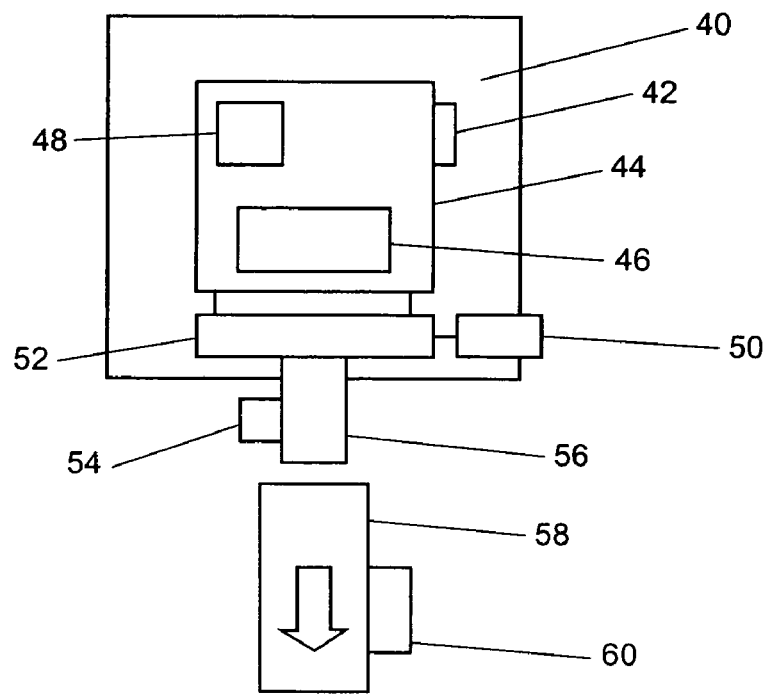
FIG. 2 is a block diagram of an ingredient storage module and an ingredient processing module of one embodiment of the invention.
Figure 3:
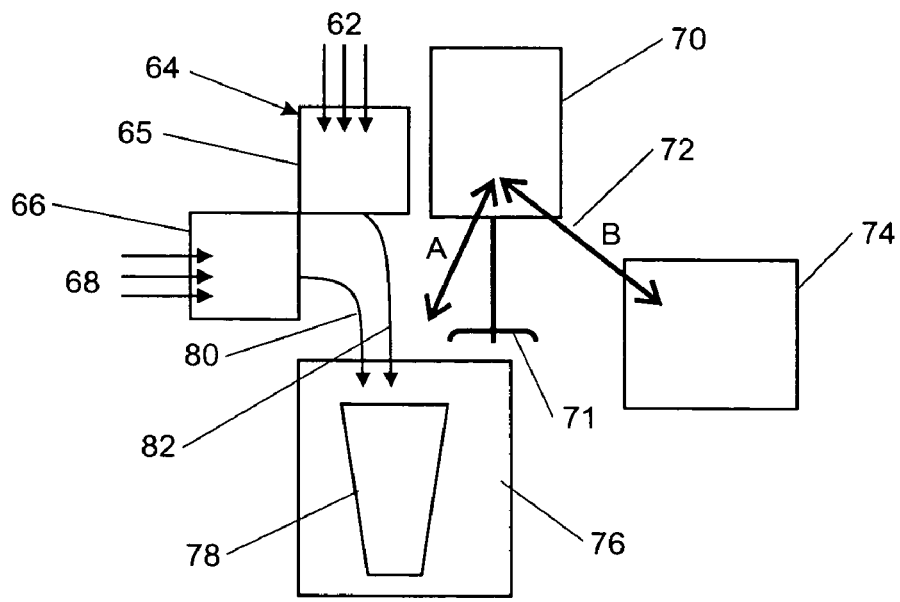
FIG. 3 is a block diagram of an embodiment of a serving dispenser for dispensing a beverage serving.

A schematic layout of one embodiment of the dispenser illustrated in FIG. 1 for dispensing nutritional beverages is illustrated in FIGS. 2 and 3.

Within an environment control unit 40 which, where required, can be hermetically sealed, there is an ingredient storage container 44 having a radio frequency identification (RFID) ingredient recognition chip 42 provided for identifying which ingredients are stored in the machine. An ingredient agitation/stirring unit 46 is provided to assist in advancing the powdered ingredients from container 44.

Also illustrated is a stock level sensor 48 to provide inventory information.

Below the storage container 44 there is provided a drive mechanism 50 which drives the feeding mechanism 52, such as an auger, which advances the ingredient from the storage container 44 into a tube 56. There is a measurer 54 on tube 56 to measure the amount of ingredient dispensed.

A chute 58 is aligned with tube 56 to receive powdered ingredients discharged from container 44. Chute 58 provided with an agitator 60 to keep powders from sticking.

Each separate ingredient has a separate storage container with the associated components just described.

Referring to FIG. 3, a powder manifold 65 is provided in communication with a source of fortificants 64 and with the sources of ingredients 62. The fortificants 64 maybe provided in a powdered form from a precise powder measuring device, or alternatively may be provided in a pre-manufactured tablet with a precise dosage. The ingredients 62 will have been discharged from a chute 58 associated with each ingredient container 44.

A liquid ingredient manifold 66 is also provided. Manifold 66 is in communication with liquid sources 68. Below the manifolds 65 and 66 is a cup dispensing mechanism 76 of the type commonly found with beverage dispensing machines. A cup 78 is illustrated. The paths of ingredients and liquids to be dispensed into cup 78 are illustrated by arrows 80 and 82.

The dispensing and processing functions are completed by the provision of a mixer drive 70 and mixer head 71 in the form of an impeller. The impeller cleaner 74 provided with an appropriate water spray nozzle is included. The impeller motor 70 and head 71 may be moved in the direction of arrow 72 A to mix the ingredients in a cup 78 or in the direction of arrow 72 B to allow for cleaning of the head or impeller 71.

In operation after the consumer has agreed to the selected nutritional beverage and the formulation algorithms have determined the quantities of ingredients required, the drive 50 actuates the feeding mechanism 52 to feed powdered ingredients through tube 56. Where required the stirring mechanism 46 ensures that the powdered ingredient is not stuck within the ingredient storage container. The amount of ingredient dispensed can be determined by a time operation of the motor 50 and/or by the measuring the amount of ingredient through measurer 54. If powdered ingredient gets stuck in chute 58 agitator 60 is able to release it.

The nature of the ingredient within storage container 44 is identified by the RFID chip 42. The level of ingredient remaining is signalled to the controller by the stock level sensor 48.

Where the ingredient requires a controlled atmosphere, such as a reduced level of moisture or oxygen, then the atmosphere within the environmental control unit 40 can be adjusted appropriately.

Ingredients 62 from ingredient storage modules 44, as illustrated in FIG. 2, together with fortificants 64 are collected in manifold 65. Liquid ingredients such as water, carbonated water or liquid flavourings are all collected in manifold 66. These are then released, usually by gravity, down pathways 80 and 82 into a cup 78. The mixer drive 70 and mixer head 71 are manoeuvred in the direction of arrow 72 A to a position where head 71 is in cup 78 and agitates the contents for a predetermined time to achieve an homogeneous mixture.

Where the ingredients have a high protein content, such as milk protein concentrate or isolate, the head 71 is operated at a reduced speed so as to avoid excess frothing.

When the predetermined mixing time is complete the drive motor 70 is raised out of the cup 76 and pivoted to position the head within the cleaning unit 74 to clean the unit.

The cup 78 is then available for the customer to remove the beverage.

Operation of Nutrition Beverage Dispenser

Figure 4:
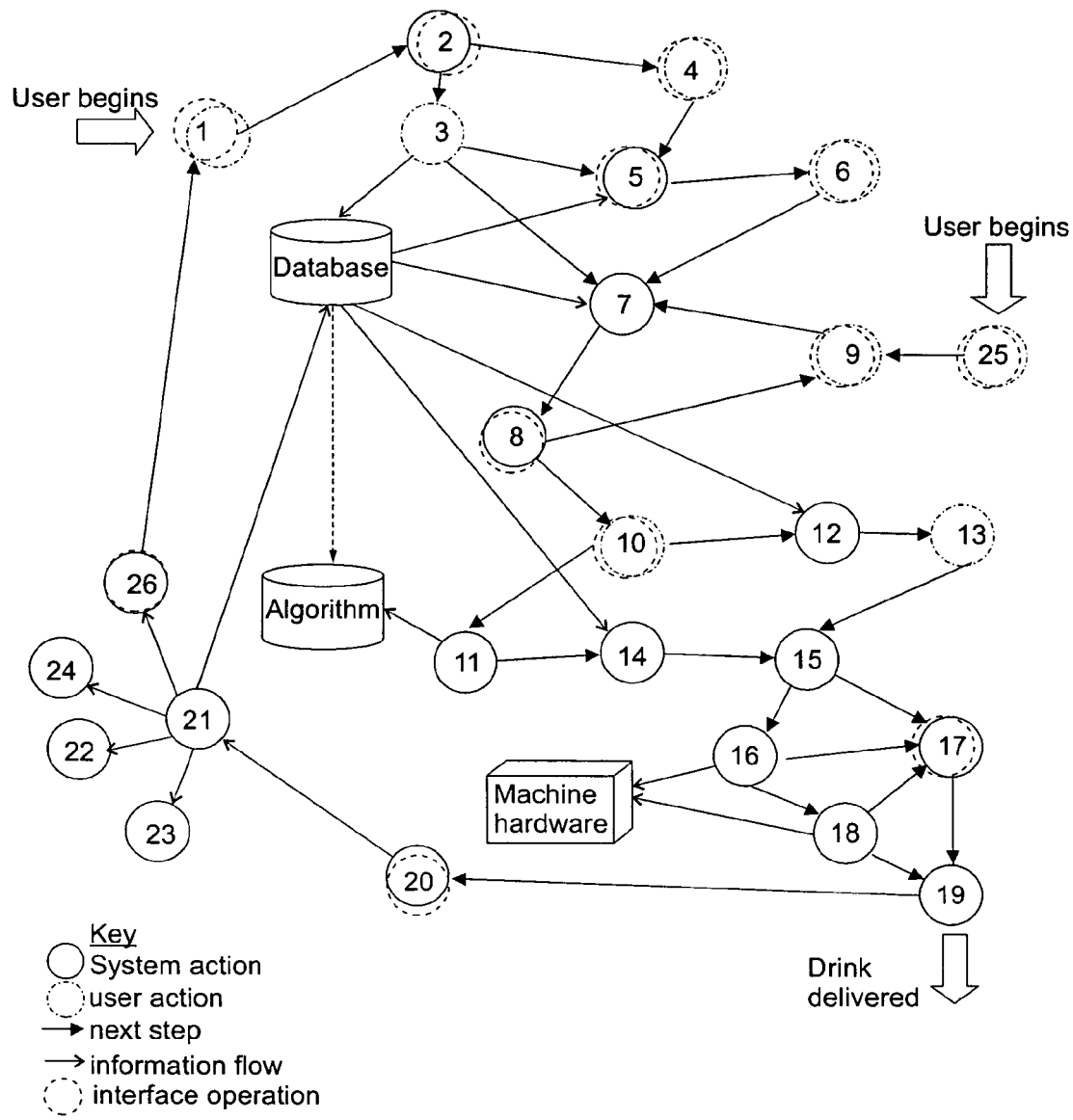
FIG. 4 is a block diagram illustrating the operation of one embodiment of a system according to the invention.

The operation sequence from the initial contact of the user through to the end of a cycle for a nutritional beverage dispensing machine of the type illustrated in FIGS. 2 and 3, is illustrated in FIG. 4 by reference to table 1 below. The numbers in the circles in FIG. 4 are not reference numbers but numbers of the step in the left column of Table 1.

Step 1 is required for a user who has not previously used the system and is not a registered member. That user may enter health information at the machine, via the internet, by mobile phone or at a membership station, which may be a user interface not integral with the dispensing machine.

At step 2 the system provides an identifier. This may be a personal identification number (PIN), information loaded onto a smartcard or information loaded onto an RFID chip in a cup to be dispensed with the beverage.

In step 3 the user's health information data is stored in the memory of the controller on the machine, on the network server or on an ID carrier, smartcard or RFID to be retained by the user.

At step 4 the user logs into the device using the interface panel on the machine, by text message, by email or through a website.

Where a user is already a member of the system they will begin at step 25 in FIG. 4. The first step is for the user to enter their ID. Then at step 5 this is verified on the interface panel, on the remote computer or on the mobile phone as the case may be.

At step 5 these user's ID is verified and their profile and preference information presented on the interface panel of the vending machine, on a remote computer or on the mobile phone as the case might be.

At step 6 the user adds any update of their health status and immediate preference details. This can be done through the user interface on the machine, by text mail or via the website as the case may be.

At step 7 the program in the computer or the server then runs the algorithm with the stored information and the updated choices through a logic system or an optimisation program.

At step 8 the beverage recommendation is presented to the user. This may be done on the interface panel of the machine, by text message, by email or on the website as the case might be.

At step 9 the user makes changes based on personal preferences and available ingredients.

At step 10 the user confirms the modified selection.

At step 11 the controller issues instructions for the ingredient storage and processing modules and the server dispenser to prepare and dispense the serving.

At step 12 the system checks for payment via a smartcard reader, by a coin drop, by direct debit or by other means associated with the machine or database.

At step 13 payment is made.

At step 14 the controller checks the sequence and delivery amounts information.

At step 15 it sends the signal to the motors and pump to deliver in the time pattern specified by the algorithm.

At step 16 the ingredients are delivered by liquid pumps, powder dispensers, tablet doses and the water supply.

In step 17 the user may be notified of the stage of preparation of the beverage as it progresses. This may be done in screen notes or by illuminating parts of the machine on the front panel.

At step 18, when the beverage is in the cup, the mixer is activated.

At step 19 when the mixer has been removed from the cup the drink ready signal is issued and the consumer then removes the drink.

In optional step 20 information about the drink formulation may be displayed. This may be displayed on the screen at the user interface or in a printed receipt. It may be printed on to a label to be affixed to the cup or it may be printed on packaging when the beverage is served in a package rather than a cup. If the serving is delivered in a package.

At step 21, information on the ingredient delivery is updated in the database for the purpose of keeping track of ingredient inventory and also to keep a record of the amounts of ingredients which the user has consumed.

At step 22 the cleaning sequence is activated so that cleaning head 71 in FIG. 3 is cleaned in head cleaner 74.

At step 23 the stock level information is transmitted to the inventory database so that restocking schedules can be prepared to ensure that the machine does not run out.

At step 24 the machine is reset to reboot the user screen and to put the ingredient dispensing module into the rest position.

The final step 26 is for the initial user prompt to join membership to appear on the interface panel.

TABLE 1

Operation Sequence for Nutrition Beverage Delivery (to be used with FIG. 4)

| | Action | Options | | | |
|---|---|---|---|---|---|
| | | a | b | c | d |
| 1 | User Joins membership enters health information | At machine | on internet | by mobile phone | at membership station |
| 2 | Machine provides ID | pin number | loads smart card | loads RFID chip in cup | |
| 3 | User health data stored | On machine | on network server | on id carrier, smart card/RFID | |
| 4 | User logs into POSI machine | on interface panel or machine hardware | by text message | by email | on website |
| 25 | Fast track usage | At machine | | | |
| 5 | User ID verified and profile and preference information presented | on interface panel | on remote computer | on mobile phone | |
| 6 | User adds current health status and momentary preference details | on interface panel | by text message | by email | on website |
| 7 | Program runs algorithm with stored information and updated choices | Logic system | Optimisation Logic Program | | |
| 8 | Drink recommendation submitted to user | on interface panel | by text message | by email | on website |
| 9 | User makes changes based on preference and ingredients | on interface panel | by text message | by email | on website |

TABLE 1-continued

Operation Sequence for Nutrition Beverage Delivery (to be used with FIG. 4)

| | Options | | | |
|---|---|---|---|---|
| Action | a | b | c | d |
| 10 User confirms selection | on interface panel | by text message | by email | on website |
| 11 Algorithms calculates drink formulation | Logic system | Optimisation Program | | |
| 12 System checks for payment | Smart card reader | coin drop | network check of database | network direct debit check |
| 13 Payment made | Smart card | account reference | direct debit | coins |
| 14 Controller checks sequence and delivery amounts information | | | | |
| 15 Motors and pump signals delivered to time pattern | | | | |
| 16 Ingredients delivered | liquid pumps | powder dispensers | tablet doser | water supply |
| 17 Information conveyed to user drink dispensing stages | On screen notes | in machine illumination | | |
| 18 mixer activated | | | | |
| 19 Drink ready signal | | | | |
| 20 Information about drink formulation displayed | On screen notes | printed receipt | label printed and added to packaging | printed on packaging |
| 21 information on ingredient delivery updated in database | ingredient storage amounts | User consumption | | |
| 22 Cleaning sequence activated | | | | |
| 23 Stock level information transmitted | telephone/text message | networked computer database | | |
| 24 machine reset | screen reboot | dosers rest | | |
| 26 User prompted to join membership | on interface panel | | | |

Pasta and Pasta Sauce Vending Device

Existing devices for preparing servings of food for dispensing from automatic vending machines can be adapted for use with the system of this invention.

One such device is described in US published patent application US 2002-0152896. The device described in that application stores pasta and the ingredients for making a pasta sauce. When a customer places an order the pasta is released into a pasta cooking pot and boiling water is added to cook the pasta. The pasta is then dispensed onto a plate. The customer selects the sauce. The ingredients, from separate storage compartments, are mixed and combined with water either prior to or after mixing with the pasta so that the customer receives a fully cooked pasta with sauce from the machine. The storage compartments for the pasta would form another component of the storage module illustrated in FIG. 1. The water dispensing and cooking functions would form a part of the processing module.

Among the ingredients to be dispensed into the sauce would be appropriate nutrients customized to the customers' health status requirements and preferences.

Boolean-Tree Algorithm for Preparation of Beverage for User

1. Introduction

A number of simple logic-trees employing information obtained from the consumer combined with nutritional and functional knowledge are used to determine the most appropriate outcome.

To demonstrate the progression through the Boolean-tree, a fictitious customer, Mike, will be followed from data entry through to the determination of the final drink demonstrating how the steps of Table 1 and FIG. 4 are done. Mike is a 46 year-old male, 6'1" tall and weighing 93 kg. He suffers from type II diabetes, and has high blood pressure and high cholesterol.

2. Initial Choices

When the consumer approaches the vending machine, there may be a number of different options for determining their beverage choice. They may want the "fast-track" option. This allows them to choose a drink base, flavour, and add desired "shots" such as "immune" or "femme". This is quick and simple, but does not make use of the major benefit of the system of the invention—the ability of the system to make specific recommendations based on the individual health profile.

The customer may have already entered their health data into the system, either during an earlier purchase at a vending machine, or possibly online at a website. If this is the case, they can simply enter their user ID and PIN, swipe their smart card, or use whatever technique is chosen to identify registered members, and the computer system in the vending machine will access the network and find the data relating to that customer.

If the customer has not yet entered their health data, they may do so at this stage. For the purpose of this example, Mike selects this option.

3. Health Profile

When the customer decides to enter their health data, they will go through an algorithm that will collect information that will be stored as their "health profile". This health profile will consist of a variety of both permanent and variable data regarding the health and general preferences of the individual. The permanent data is collected and stored as fixed information, while the variable data may be automatically set to a default but is able to be changed each time the vending machine is used.

Figure 5:
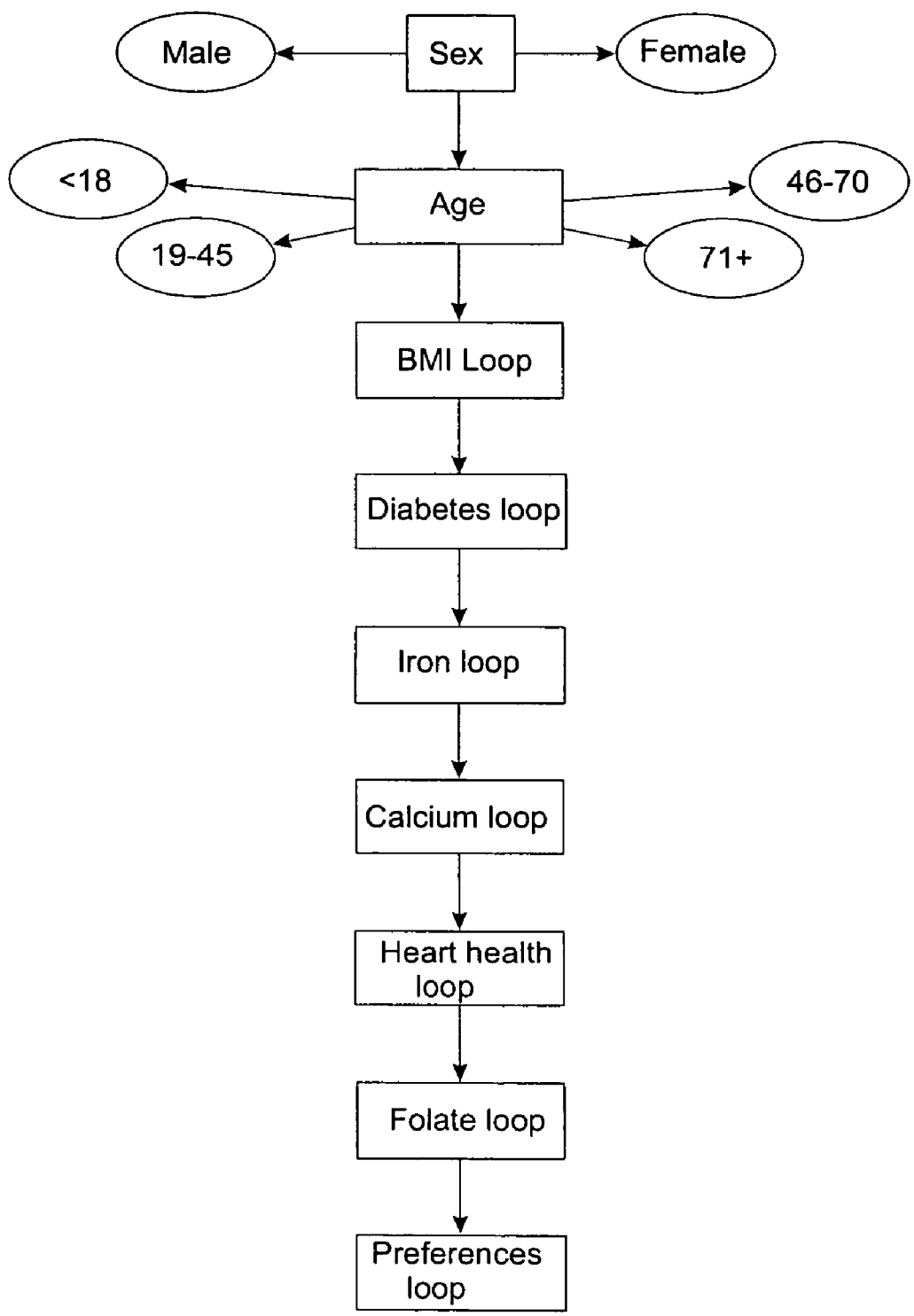
FIG. 5 is a block diagram of a health profile algorithm.

A typical flow-chart outlining the type of information and options that may be used to collect information for the health profile is shown in FIG. 5 with the individual loops shown in FIGS. 6 to 11. These are representative questions that may be used. When the machine is intended to be used with classes of users, for example school children or the elderly, the questions would be tailored to the user group.

The first questions are relatively self-explanatory, and seek information on the customer's sex and age. The age brackets are based on similar nutritional needs and may be broken into smaller ranges to ensure the consumer feels comfortable about the question. Mike is male, and between 46-70 years of age.

BMI Loop

Figure 6:
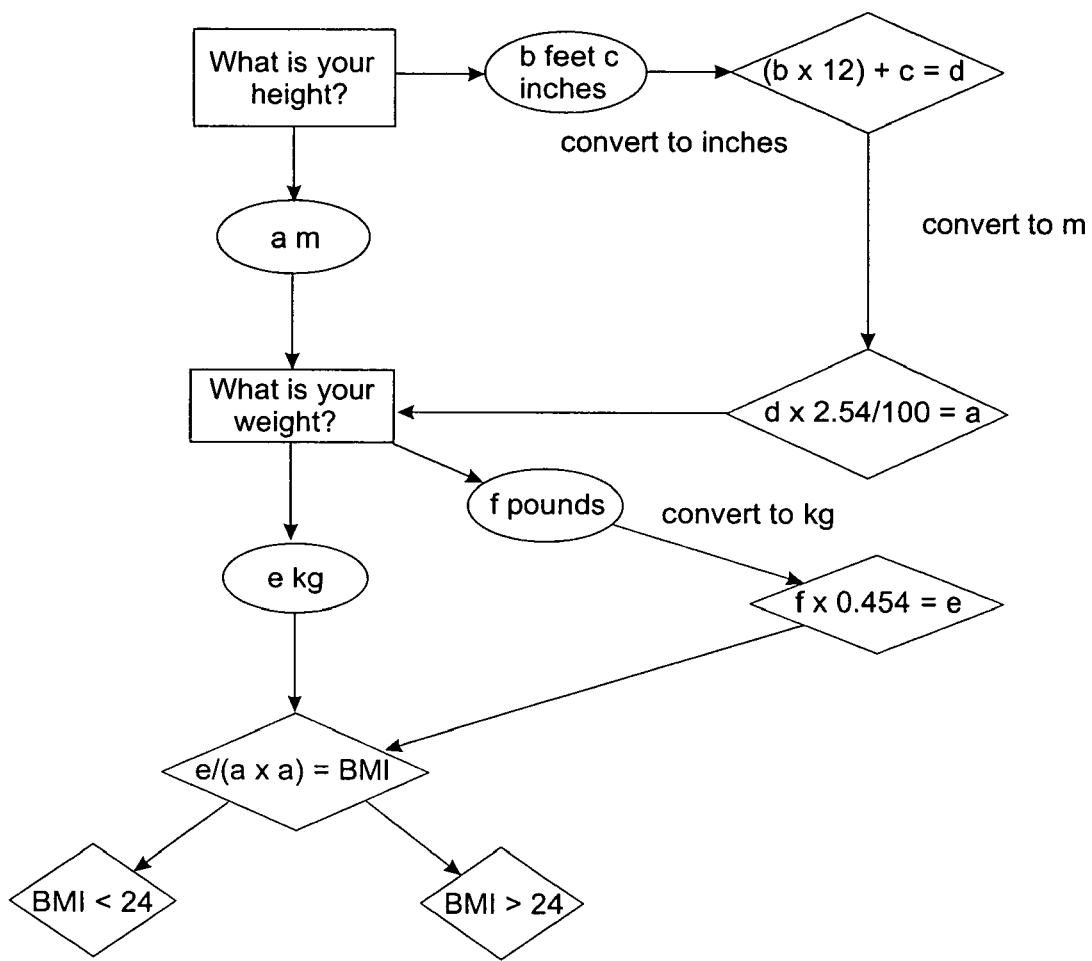
FIG. 6 is a block diagram of a process loop for determining body mass index.

Referring to FIG. 6, an individual's body mass index (BMI) is measure of body fat based on height and weight, and is an important indicator of risk for a variety of health concerns. The BMI is calculated by dividing the person's weight in kilograms by the square of their height in meters. The BMI loop calculates the BMI based on information provided by the consumer, allowing for the figures to be entered either in metric or imperial units. Generally, a BMI greater than 25 is an indication that a person is overweight. However, people tend to over-estimate their height and under-estimate their weight, and so a BMI greater than 24 has been used as a cut-off. The height and weight of a consumer could also be measured at the machine through the use of currently-available technology and BMI calculated by the measuring device.

Mike's BMI is calculated from his height (6'1") and weight (93 kg) as follows:

Height in meters=$((6 \times 12)+1) \times 2.54/100 = 73 \times 2.54/100$ 1.85 m $BMI = 93/(1.85 \times 1.95)$ 27.2

Therefore Mike fits into the 'BMI>24' category.

Diabetes Loop

If a person has either type I or type II Diabetes, either the body does not produce enough insulin or the cells ignore the insulin. Insulin is necessary for the body to be able to use sugar. When glucose builds up in the blood instead of going into cells, it can cause a variety of problems. Therefore, it is important for people with diabetes to control their sugar intake. Different sugars have different effects on blood glucose levels, with sucrose and glucose having the largest effect. Effectively calorie-free sweeteners like aspartame, saccharin, sucralose and acesulfame-K will not increase the blood glucose level, but the sugar alcohols (xylitol, mannitol, and sorbitol) have some calories and will increase blood glucose slightly. It is also important to consider overall carbohydrate intake, as calorie for calorie, all digestible carbohydrates raise blood glucose about the same amount (American Diabetes Association, 2005). There is also evidence that eating a healthy diet with a low level of sugars may help delay the onset of the disease in those with risk-factors for developing type II diabetes.

Figure 7:
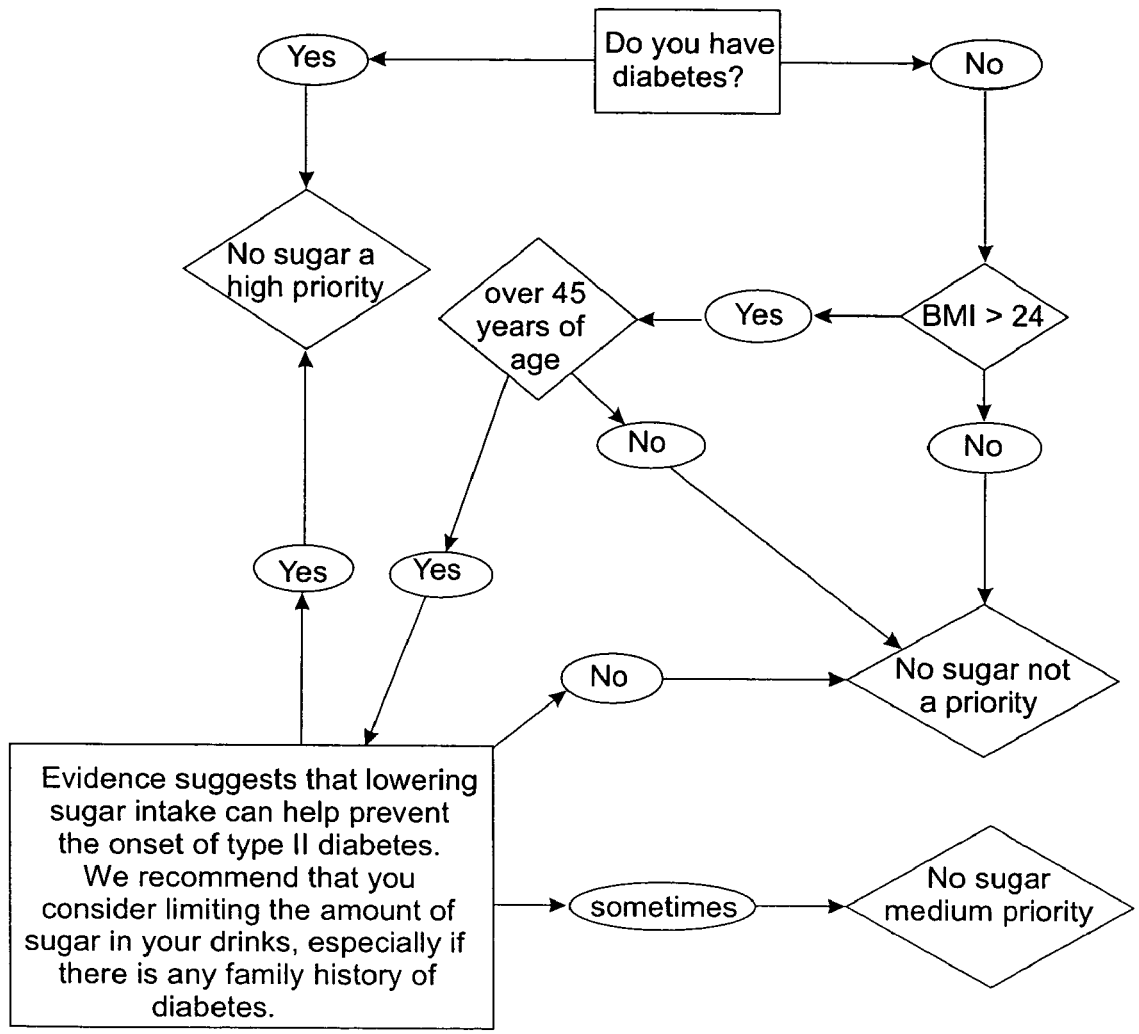
FIG. 7 is a block diagram of a loop for processing information of relevance to diabetes.

The diabetes loop shown in FIG. 7 shows an example of possible questions and outcomes that take into account whether an individual has diabetes or some of the potential risk factors.

Mike does have type II diabetes, so he would be assigned a high priority for no-sugar. This requires that drinks must not contain any sucrose or glucose, and must not have a total sugars content of more than 5%. If he had not been diagnosed with diabetes, the logic-tree would have registered that he was over 45 years of age and had a BMI greater than 24 and would have suggested that he consider choosing to make no sugar a high priority. The customer may over-ride the nutritional recommendations with this example, but warnings will be displayed to ensure they are aware that their decision is against nutritional advice.

The other two priority levels are medium and low. A medium priority means that a constraint will be placed upon the drinks recommended by the system to ensure that the total sugars present will not exceed 10%. A low priority for no sugar means that the amount of sugar will not influence any decisions made regarding which drink to recommend to the customer.

Iron or Calcium Loop

Inadequate dietary intakes of iron and calcium are commonplace among women in many western countries, and have been implicated in development of problems such as anemia and osteoporosis. However, it is not desirable to give extra dietary iron to males or to women already taking iron supplements.

Figure 8:
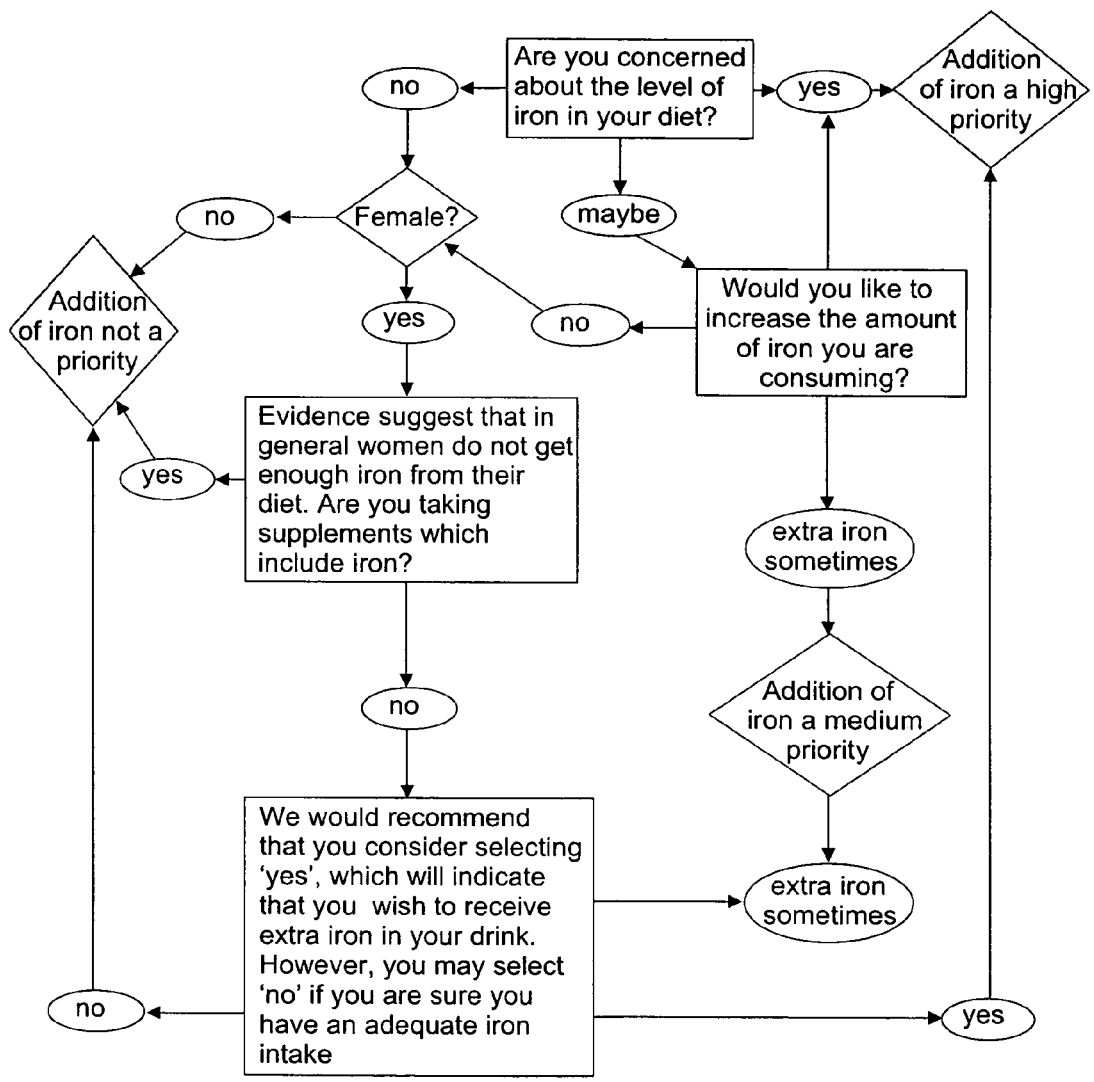
FIG. 8 is a block diagram of a loop for processing information concerning iron in the diet.

The iron loop in FIG. 8 allows a customer response to a question regarding their iron intake to be accepted or queried based on other aspects of their health profile. If the customer says that they are not concerned about their iron intake, the system checks their sex and if they are female, posts a message explaining that women tend to be low in iron. It enquires whether the individual is taking a supplement that contains iron, and if they aren't, another message is presented that strongly recommends that the customer consider making iron a high priority. A high priority for iron means that the system will include extra iron in the drink unless specifically directed otherwise by the consumer; a medium priority means that iron will be added unless it conflicts with a higher priority instruction; and a low priority will not result in the addition of iron unless the customer specifically asks for it. A similar loop is used for calcium.

Mike is unlikely to be concerned about the level of iron or calcium in his diet, and as he is a male, the system will avoid the message system and simply assign both iron and calcium a low priority.

Heart Health

Figure 9:
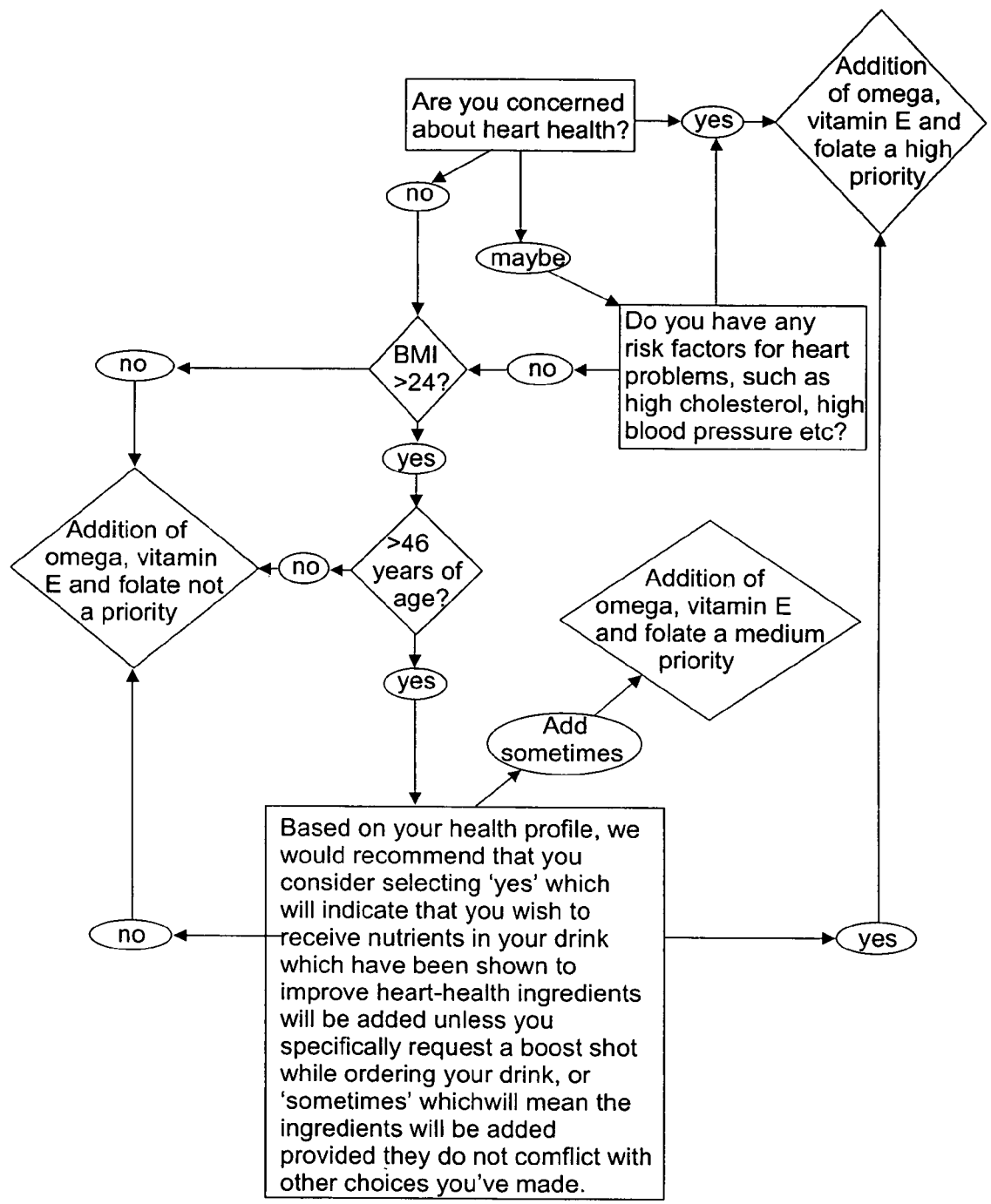
FIG. 9 is a block diagram of a loop for processing information of relevance to heart health.

In the western world there are increasing numbers of people suffering from conditions such as atherosclerosis. Research has identified a variety of micronutrients which appear to improve heart health, including antioxidants (vitamin E), omega-3 fatty acids, and folic acid. A loop for heart health is shown in FIG. 9.

With his current health status, Mike should be concerned about heart health. However, if he was unsure, this loop prompts him to consider possible risk factors he may have. Even if Mike is totally unaware of the strain his heart may be under, the logic tree examines his health profile and registers that he is over 45 years of age and has a BMI greater than 24. Based on this information, a recommendation message is presented which prompts Mike to make heart health a high priority. This would ensure that the heart health ingredients will be added to all his drinks unless he specifically over-rides that instruction.

At present, this heart-health loop refers to a single "heart shot" made up of three components—omega-3, vitamin E and folate. Whatever choice an individual makes with regard to heart health priority, it is applied to the group of ingredients rather than the individual components. In an alternative, this is changed to consider the separate ingredients instead, allowing greater flexibility in meeting consumer needs. Such an alternative requires more ingredient streams and more input from the consumer.

Folate Loop

Figure 10:
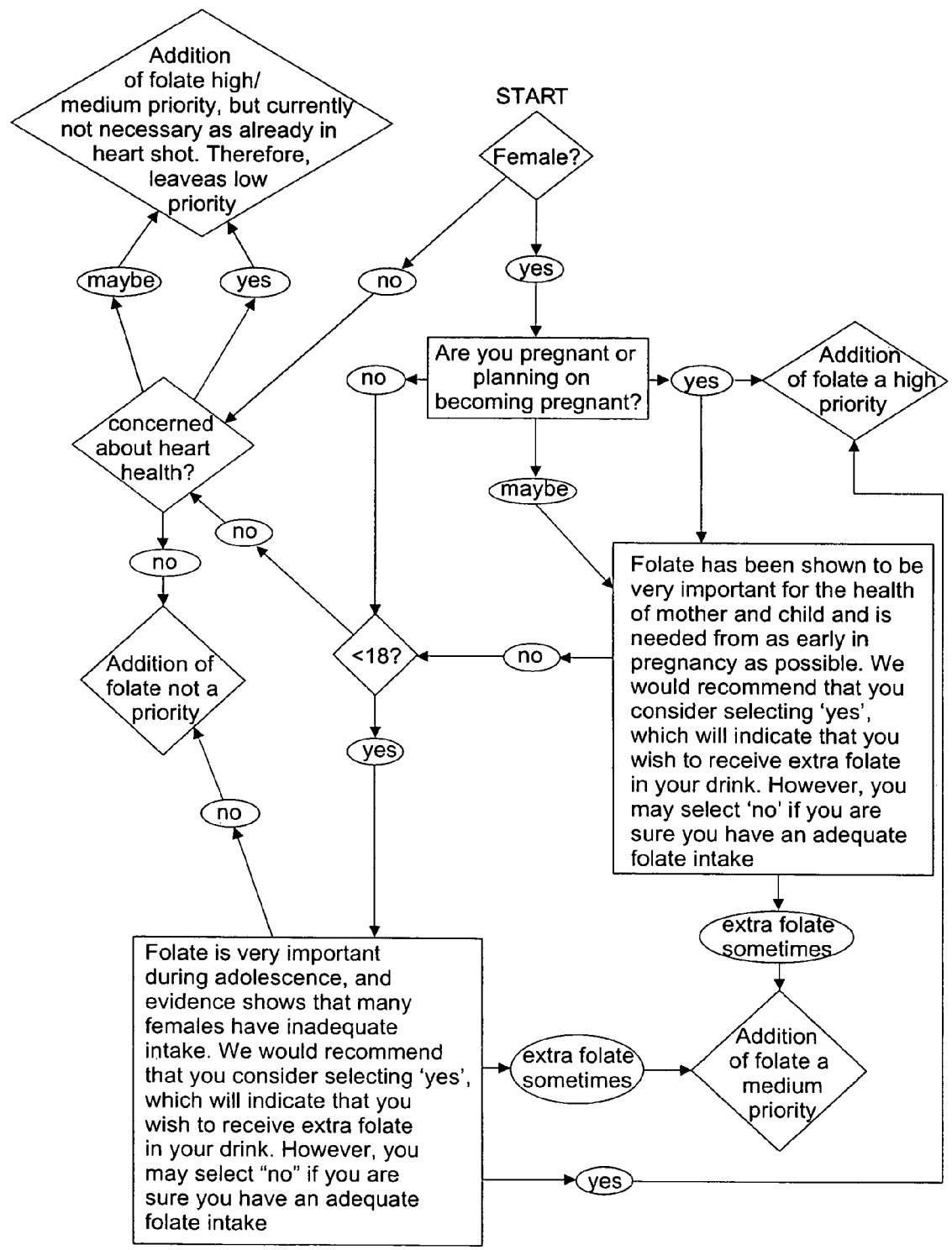
FIG. 10 is a block diagram of a loop for processing information concerning folate.

As well as being involved in heart health, folate is also very important in women's health, especially during adolescence and pregnancy. The folate loop in FIG. 10 is only shown to customers who are female.

The system of this example operates in terms of "bases" and "shots", and "heart health" corresponds to a single shot. Therefore, since the folate is included in the "heart shot" there is no point in having it set to high priority on an individual basis. In a system where the "shots" approach is not used the folate loop would need to be adjusted accordingly.

As Mike is male, the system will not show him the folate loop. He will already be getting extra folate from his decision to make heart health a high priority.

Personal Preferences Loop

Figure 11:
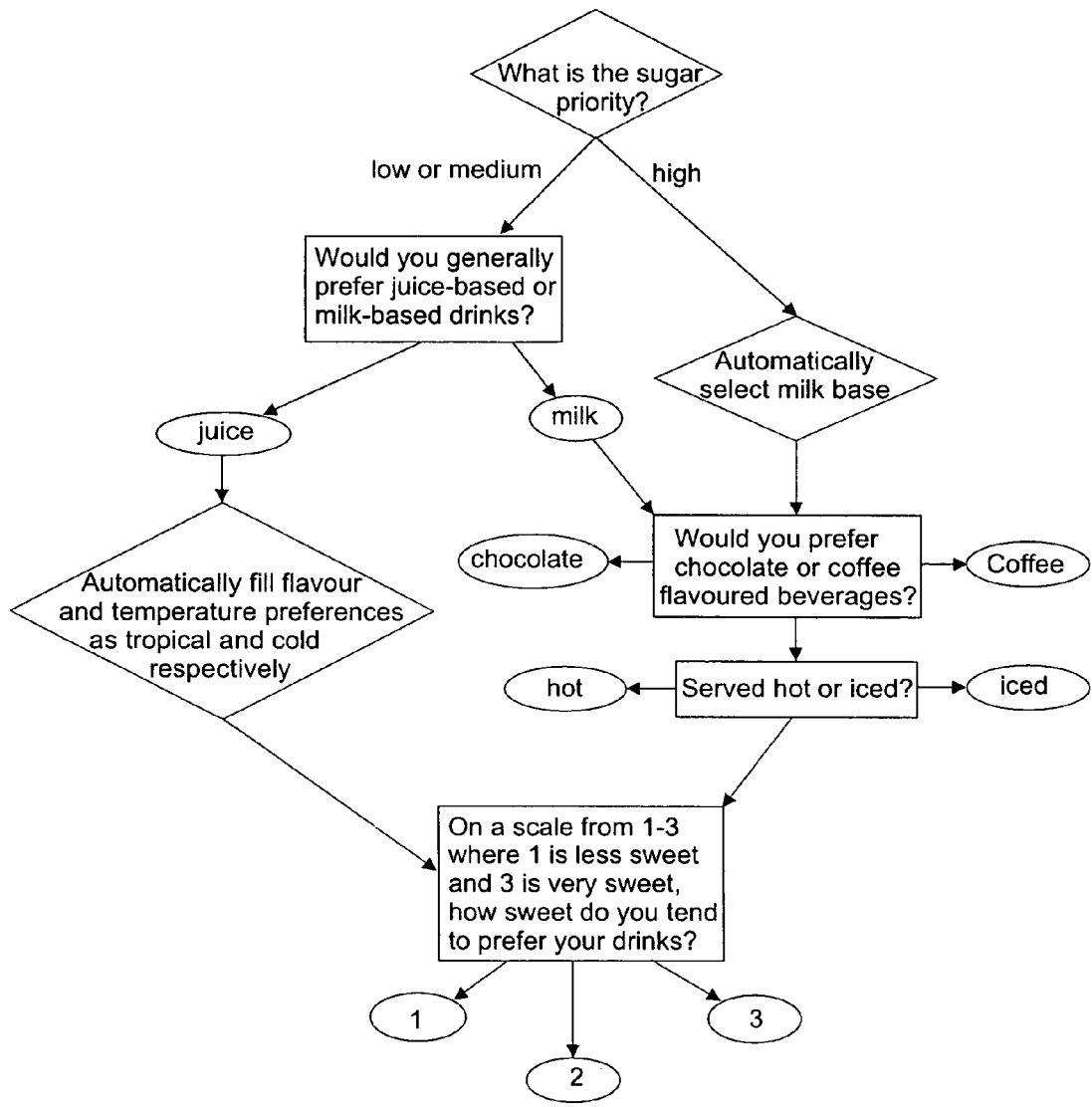
FIG. 11 is a block diagram of a loop for processing customer requests for personal preferences.

The final loop in this section of the health, illustrated in FIG. 11, is about personal preferences. The logic tree is able to restrict the drink choices presented based on the customer health profile (i.e. no sugar priority), but the customer is able to have a certain amount of input into the type and flavour of drink that will be recommended by the system. In other examples where more drink types and flavours are added to the system this part of the logic tree will be substantially larger.

Mike has no sugar as a high priority, so automatically will have a milk-based drink set as his default. He prefers hot chocolate, and has a bit of a sweet-tooth so chooses a sweetness level of 3. Artificial sweeteners are used Mike can still have it extra sweet without compromising his diabetic condition.

4. Choice

Once a customer has entered their health profile, either at the vending machine or online, the system will recognise them and be able to call up their specific information from the databases. In this example a record is kept of a customer's history of choices, including their favourite drink, the times and places that vending machines are commonly accessed, and their usual daily intake of various nutrients.

Figure 12:
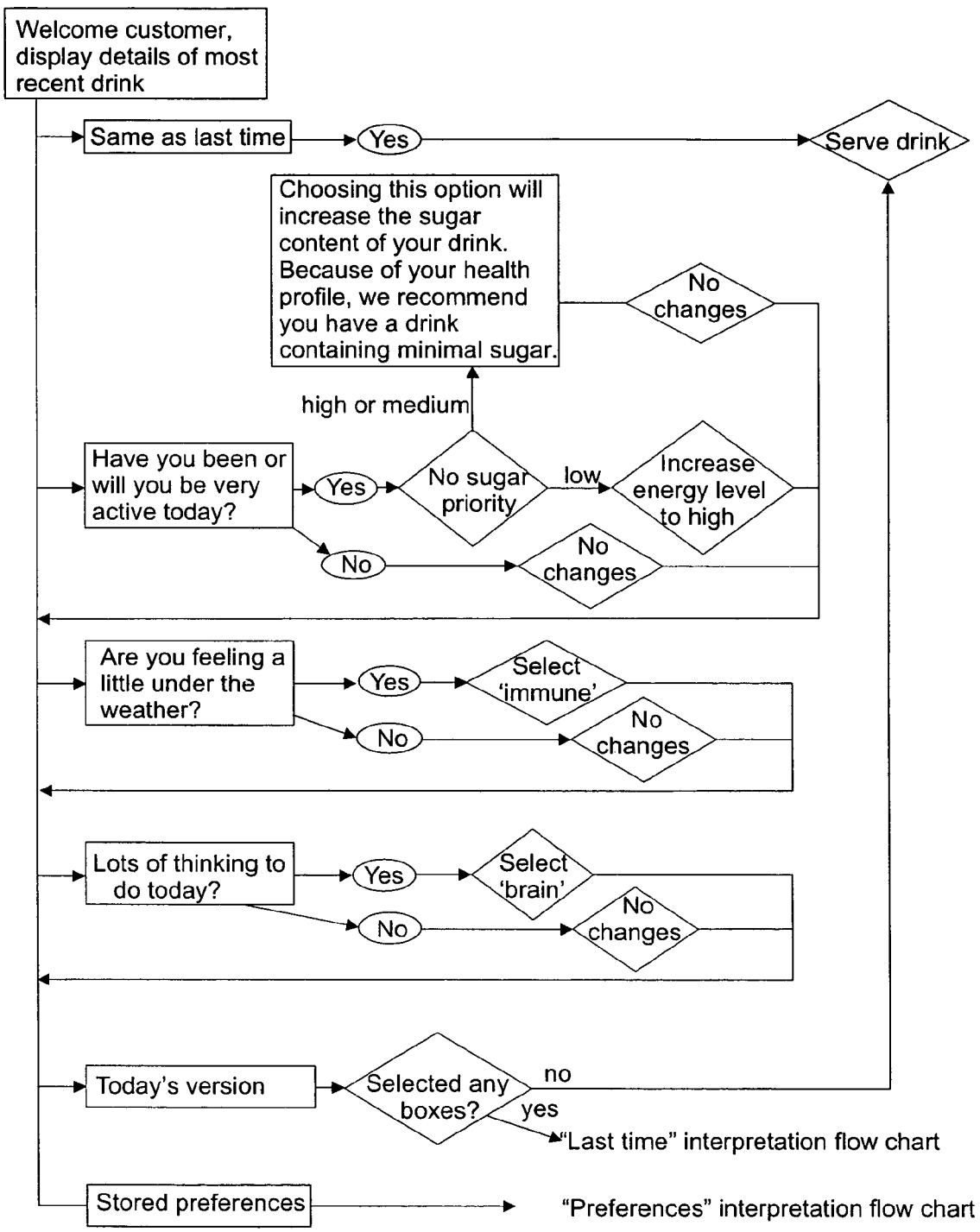
FIG. 12 is a block diagram for processing servings according to customer preferences.

FIG. 12 is a logic tree approach for someone who has entered their health data logs into a vending machine. The customer is welcomed, and if they have used the system before, they can be offered the same drink as they had last time as a quick choice. Other options include answering some 'variable data' questions on the customer's current health or status, which may change the health profile and thus the drink recommendation. The customer can then either ask for an updated version of their last drink ("today's version") or a drink based on their stored health profile/preferences information ("stored preferences").

Mike has not used the system before, so he has no history data to allow him to chose the "same as last time" or "today's version" options. He answers "no" to each of the three questions, then presses the "stored preferences" button.

The answers to the 'variable data' questions is combined with that stored in the customer's health profile, and the system works through a further logic tree to determine what the drink is that most closely matches the requirements of the customer's health status and the customer's personal preferences. An example of such a logic tree is shown in FIG. 13.

Figure 13:
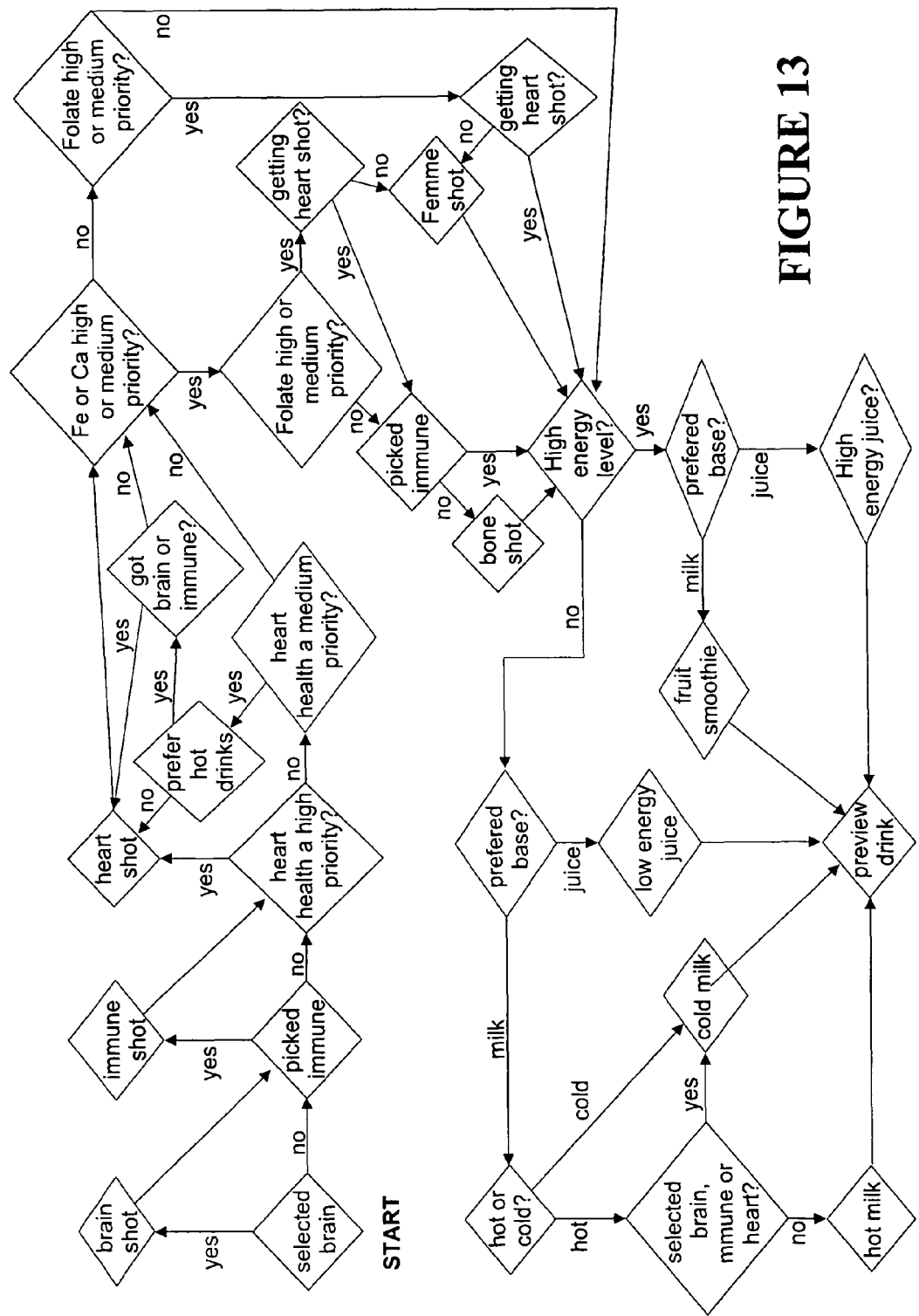
FIG. 13 is a block diagram of an interrogation for processing information to provide a customer with a drink accommodating both health profile and preferences.
Figure 14:
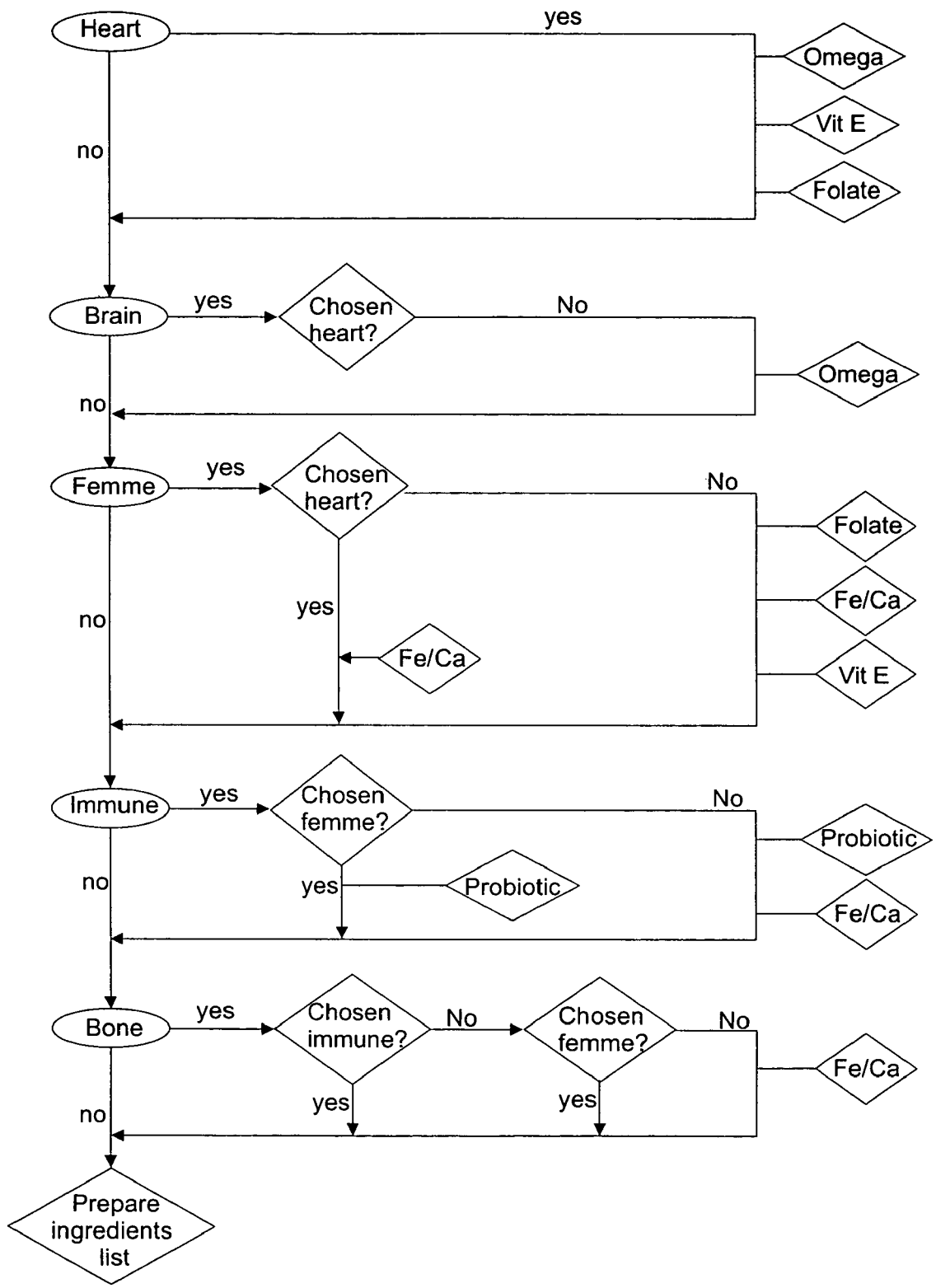
FIG. 14 is a block diagram of an interrogation for ensuring that the ingredients selected and chosen are incorporated into the beverage to be served.

Working through the FIG. 13 logic tree for Mike, he did not select brain or immune. Heart health was a high priority, so he will get the heart shot. Neither iron nor calcium were high priority, and the energy level is to be kept low. His preferred base was milk, and he likes it hot. However, he is getting the heart shot, which means that he must have it in a cold beverage. The preferences for chocolate and extra sweetness are not affected by this change. To see the actual ingredients that each shot corresponds to, and to ensure that a selection of two shots which overlap in ingredients does not cause a double dose of any ingredient to be added to the product, FIG. 14 is used. The final recommended drink is an extra sweet iced chocolate milk-based beverage (low calorie and low in sugar) with added vitamin E, folate and omega-3 for heart health.

Mike is presented with this recommendation, and given the option of changing the flavour, shots, temperature and base. However, should any of his changes produce a drink which goes against the recommendations based on his health profile, a message explaining this will be shown. If Mike then decides to over-ride the recommendation he does so in an informed manner.

Now that Mike a 'history' with the system, he can use the "same as last time" or "today's version" options shown on FIG. 12. Today he feels like he may be coming down with a cold, and so he answers 'yes' to the 'are you feeling under the weather' question. This stimulates the system to add the Immune shot to Mike's drink. Mike then presses the "today's version" button.

Figure 15:
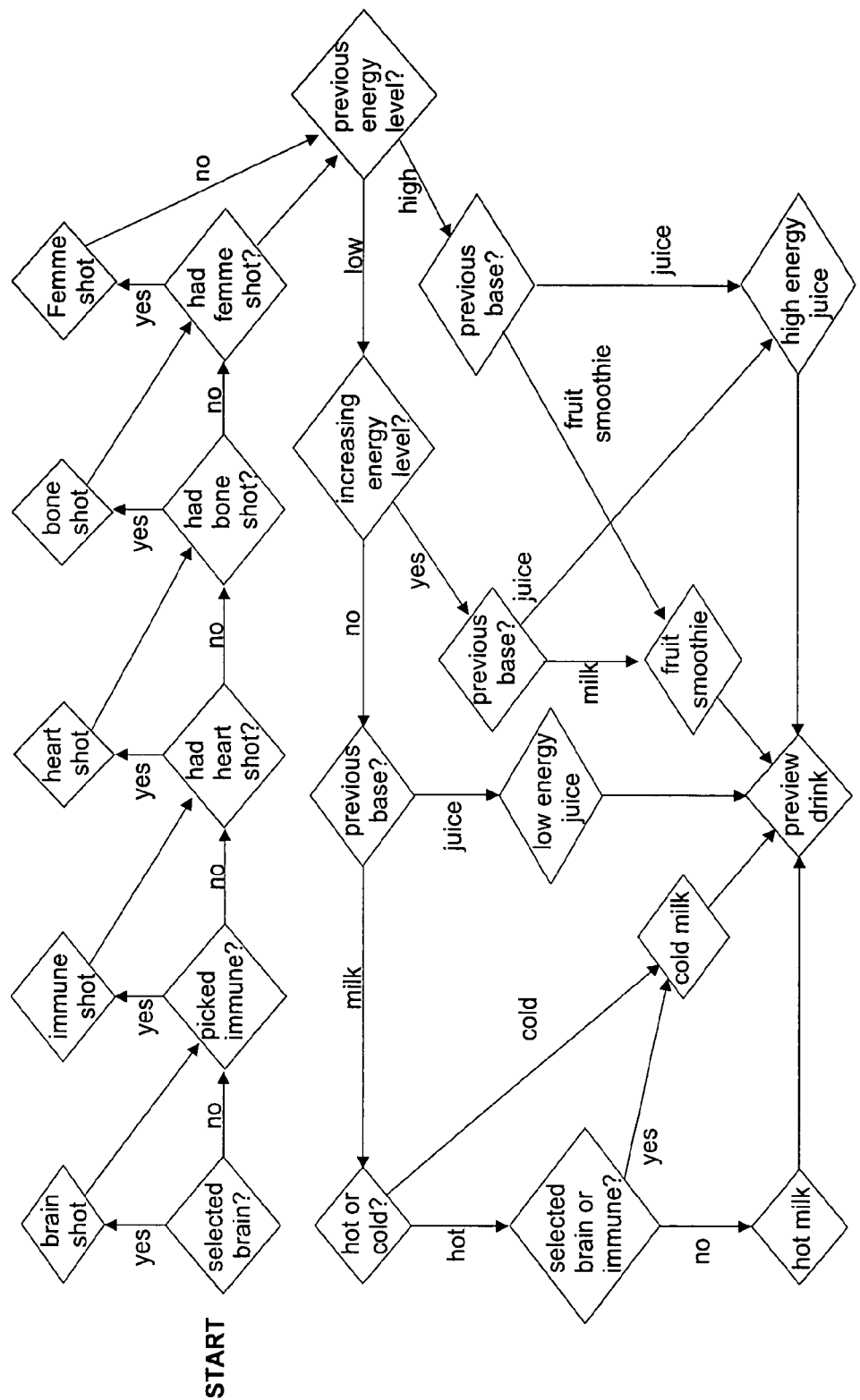
FIG. 15 is a block diagram of an interrogation for determining the drink to be served based on consumer history.

The system can access the record of the drink Mike had last time, and so a simpler logic tree is able to be used this time (FIG. 15). Working through this example for Mike, he did not select brain but he did ask for the immune shot. He did receive the heart short last time, but not the bone or femme shot. He hasn't asked for the energy level to be increased so it is to be kept low like last time. Neither iron nor calcium were high priority, and the energy level is to be kept low. His previous base was an extra-sweet chocolate milk, and since it was already cold it is not going to be affected by the addition of the immune shot. Again using FIG. 14, the final recommended drink is an extra sweet iced chocolate milk-based beverage (low calorie and low in sugars) with added vitamin E, folate, and omega-3 for heart health, and a probiotic with extra calcium and iron for an immune boost.

Just in case what Mike thought he had last time wasn't what he really did, he is presented with the summary of the beverage, and can choose to change the flavour, shots, temperature and base in a similar manner to last time.

A summary of five consumers (including Mike) with the permanent information in their health profile, their personal choices, and their responses to the variable data questions for that day is shown in Table 2. The interrogation set out in FIG. 13 has been used to determine the best drink to recommend for each individual based on this information, and this is shown in Table 3.

The individuals were all given the option to change the recommended drink, and their final choices are outlined in Table 4. The compositions calculated from the final choices are set out in table 5.

TABLE 2

| Health profiles and drink recommendations | | | | | |
|---|---|---|---|---|---|
| | Sam | Mike | Matt | Carolyn | Sarah |
| Permanent data in profile | | | | | |
| Sex | Male | Male | Male | Female | Female |
| Age | 19–45 | 46–70 | <18 | 19–45 | 19–45 |
| BMI | <24 | >24 | <24 | <24 | >24 |
| No sugar | Low | High | Low | Low | Low |
| Iron | Low | Low | Low | High | High |
| Calcium | Low | Low | Low | Medium | High |
| Heart health | Low | High | Low | Low | Low |
| Folate | Low | Low | Low | Low | High |

TABLE 2-continued

Health profiles and drink recommendations

|  | Sam | Mike | Matt | Carolyn | Sarah |
|---|---|---|---|---|---|
| Base preference | Juice | Milk | Milk | Juice | Milk |
| Flavour | Tropical | Chocolate | Chocolate | Tropical | Coffee |
| Temperature | Cold | Hot | Cold | Cold | Hot |
| Variable data |  |  |  |  |  |
| Today's activity | Low | Low | High | Low | Low |
| Immune | Low | Low | Low | High | Low |
| Brain | Low | Low | High | Low | Low |

TABLE 3

Recommended drinks based on FIG. 12 interrogation

|  | Sam | Mike | Matt | Carolyn | Sarah |
|---|---|---|---|---|---|
| Energy | High | Low | High | Low | Low |
| Base | Juice | Milk | Fruit smoothie | Juice | Milk |
| Flavour | Tropical | Chocolate | Tropical | Tropical | Coffee |
| Temperature | Cold | Cold | Cold | Cold | Hot |
| Heart | No | Yes | No | No | No |
| Brain | No | No | Yes | No | No |
| Femme | No | No | No | No | Yes |
| Immune | No | No | No | Yes | No |
| Bone | No | No | No | No | No |

TABLE 4

Drinks as changed by the consumers

|  | Sam | Mike | Matt | Carolyn | Sarah |
|---|---|---|---|---|---|
| Energy | High | Low | High | Low | Low |
| Base | Juice | Milk | Fruit smoothie | Juice | Milk |
| Flavour | Tropical | Chocolate | Tropical | Tropical | Coffee |
| Temperature | Cold | Cold | Cold | Cold | Hot |
| Heart | No | Yes | No | No | No |
| Brain | No | No | Yes | No | No |
| Femme | No | No | No | No | Yes |
| Immune | No | No | No | Yes | No |
| Bone | No | No | No | No | Yes |

TABLE 5

Calculated compositions of beverages for each health profile

| Composition | Sam | Mike | Matt | Carolyn | Sarah |
|---|---|---|---|---|---|
| Water (g) | 321.141 | 356.608 | 315.361 | 344.386 | 351.075 |
| Protein (g) | 25.1 | 20.401 | 25.338 | 20.05 | 20.246 |
| Fat (g) | 0.083 | 0.854 | 0.87 | 0.066 | 0.467 |
| Saturated fat (g) | 0.056 | 0.367 | 0.387 | 0.045 | 0.314 |
| Total carbohydrates (g) | 49.425 | 16.827 | 51.845 | 29.704 | 20.703 |
| Carbohydrate not fibre (g) | 39.008 | 11.328 | 42.283 | 21.996 | 15.703 |
| Fibre (g) | 10.418 | 5 | 9.063 | 7.709 | 5 |
| Complex carbohydrate (g) | 0.058 | 0.32 | 0.058 | 0.107 | 2.475 |
| Sugar (g) | 38.95 | 10.544 | 42.224 | 19.541 | 10.544 |
| Lactose (g) | 0.221 | 11.129 | 13.178 | 2.525 | 13.235 |
| Ash (g) | 3.385 | 4.341 | 5.616 | 4.906 | 6.628 |
| Energy (kJ) | 1251.22 | 655.347 | 1325.4 | 834.583 | 702.041 |
| Energy from fat (kJ) | 3.126 | 32.171 | 32.793 | 2.501 | 17.586 |
| Ca (mg) | 286.902 | 777.335 | 946.79 | 538.241 | 1060.65 |
| K (mg) | 1304.69 | 499.153 | 875.403 | 993.081 | 569.853 |
| P (mg) | 185.373 | 130.125 | 130.125 | 174.324 | 136.185 |
| Na (mg) | 60.7735 | 89.903 | 109.5 | 48.6188 | 88.3 |
| Cl (mg) | 5.6354 | 0.1106 | 0.1106 | 4.5305 | 0.1106 |
| Fe (mg) | 0 | 0 | 0 | 4.5214 | 4.6096 |
| Mg (mg) | 115.852 | 99.9907 | 111.839 | 107.825 | 106.339 |
| Zn (mg) | 3.7496 | 3.7496 | 3.7496 | 3.7496 | 3.7566 |
| Vitamin A (mg) | 0.1746 | 0 | 0.1309 | 0.0873 | 0 |
| Vitamin C (mg) | 295.932 | 14.9986 | 225.699 | 170.537 | 30.07 |
| Vitamin D (mg) | 0.0025 | 0.0025 | 0.0025 | 0.0025 | 0.0025 |
| Vitamin E (mg) | 0 | 5 | 0 | 0 | 5 |
| Thiamin (mg) | 0.375 | 0.375 | 0.375 | 0.375 | 0.375 |
| Riboflavin (mg) | 0.425 | 0.425 | 0.425 | 0.425 | 0.425 |
| Niacin (mg) | 4.9995 | 4.9995 | 4.9995 | 4.9995 | 4.9995 |
| Vitamin B6 (mg) | 0.5 | 0.5 | 0.5 | 0.5 | 0.5 |
| Folate (mg) | 0 | 0.1 | 0 | 0 | 0.1 |
| Vitamin B12 (mg) | 0.0015 | 0.0015 | 0.0015 | 0.0015 | 0.0015 |
| Pantothenic acid (mg) | 2.4998 | 2.4998 | 2.4998 | 2.4998 | 2.4998 |
| Caffeine (mg) | 0 | 0 | 0 | 0 | 62.84 |
| Omega 3 (mg) | 0 | 99.96 | 99.96 | 0 | 0 |
| EPA + DHA (mg) | 0 | 79.968 | 79.968 | 0 | 0 |
| Probiotic (x10^9 cfu) | 0 | 0 | 0 | 5 | 0 |

Optimising Servings According to Nutritional Content, Preference and Cost

Outline of Problem

The user's health status is determined from information obtained from them by the method described with reference to FIGS. 5 to 11 or in any other way. Each health status is associated in a database with nutritional preferences as defined by nutritionists. Customer preferences such as flavour, solid or liquid or other are also defined by the user as described with reference to FIG. 12 or in any other way.

An optimisation routine formulates a recipe for a serving based on these preferences, made optimal by means described in the Objective Function section below.

Features of the overall recipe may also be defined as functions of the amounts of each component and property in the recipe. In one embodiment some flavour characteristics are features. In another embodiment viscosity is a feature. In another embodiment glycaemic index is a feature.

The recipe for a serving to be dispensed is a combination of various streams in certain proportions. The streams themselves are made up of varying numbers of ingredients. Each ingredient has physical components (such as calcium content) as well as intangible properties (such as energy content, organic status, or genetically modified status).

Combining these is first formulated as an optimisation problem. Solution methods that may be applied to the problem are described.

Problem Formulation

Variables

Variables representing amounts of each stream in the recipe are defined. In one embodiment some streams are available only in discrete units (such as tablets containing a known amount of vitamin E). In this case the variables corresponding to these streams are discrete. For instance, if $x_9$ corresponds to a stream that is available only in 0.3 g tablets, then $x_9$ should be an integer variable representing the number of discrete units in the recipe. The total weight in grams of these tablets in the recipe is then $0.3x_9$.

Further variables required are defined as the amounts of each component and property that have been consumed on a particular day, prior to the current serving.

In one embodiment binary variables are defined indicating whether each stream is used in the recipe or not. Non-negative integer variables $y_i <= 1$ are thus required for each stream, where i is a number corresponding to a particular stream.

All variables are defined, in one embodiment, with finite upper bounds. The amount of any stream in the recipe is limited by the size of the recipe. Binary inclusion variables are obviously bounded above by 1. The amounts of each component and property already consumed on a day might theoretically have no bound, but the variables representing this are defined to have upper bounds. If more than this upper bound has actually been consumed then the variable will be assigned the value of the upper bound. In the case where the amount of a component or property in a serving is bounded above, the upper bound is set to the maximum amount of that component or property permissible in a serving. Otherwise a suitably large value is chosen that bounds daily consumption from above.

Objective Function

In one embodiment penalty weightings are applied to each nutritional and flavour intensity preference so that satisfaction of the preference attracts no penalty but deviation from the preference is awarded a number of penalty points. The objective is to minimise nutritional and flavour intensity penalty points and total cost. Other factors may be identified and incorporated in the same way that nutritional and flavour preferences and total cost are combined.

Penalty points are awarded as follows. For each component or property of the ingredients, and for each feature of this recipe a target value for the level of that component or property or feature is specified. A range either side of this value is allowed with no penalty. Every unit by which a recipe fallsoutside this range incurs a number of penalty points given by a function of the amount of that component or property or feature in the serving. In one embodiment this function is convex.

A positive weighting is assigned to penalty points incurred by deviation from the target value of each component or property or feature and to the overall cost. The objective function is to minimise the total of all weighted penalty points and the weighted cost.

In one embodiment all weightings assigned to penalty points incurred because of nutritional targets are made so large relative to other weightings that nutritional targets are prioritised absolutely over other targets such as flavour and cost. This is possible since the values of each variable and thus the deviations of each variable from any fixed target are bounded.

In one embodiment all weightings assigned to penalty points incurred because of flavour targets are made so large relative to other weightings that flavour targets are prioritised absolutely over other targets such as cost.

In another embodiment weightings assigned to penalty points incurred because of each target are made such that the one group of targets is prioritised partially over another.

In one embodiment the relative priorities are set by the user. The degree of weighting placed on nutrition, flavour and cost are standardised to sum to 100. Values of each can be changed directly by the user.

In one embodiment the relative priorities are represented by the position of a point in a triangle on the screen, with corners labelled "Nutrition", "Flavour" and "Cost". The user selects a point in the triangle. The distance from that point to each corner is calculated and the relative priorities thus determined by some monotonic function of the distances are displayed. The user can switch between direct adjustment of the weightings and movement of the point in the triangle, observing in real time how each affects the other.

According to one embodiment, nutritionists will have chosen certain relative priorities and optimised the recipe for each health status (or perhaps each health status/flavour preference combination), storing the results in a database. The resulting recipe is then immediately available as a preset selection for users matching that profile.

Constraints

For each component and property or feature a minimum and maximum can be specified. These are absolute limits desired on the total amount of certain components or properties or features in the serving. Not all components and properties and features may require explicit limits on minimum or maximum amount per serving.

There are also daily minima, maxima and objective function penalties, entirely analogous except that to the amount of each component or property or feature in the current recipe is added the variable representing the current daily amount of that component or property or feature.

Further constraints for each component and property and feature are required in order to assign the penalties used in the objective function.

Penalties are applied as follows. Suppose the amount of a component or property or feature in a recipe is c and the target value is t. Define positive variables p+ and p−. Then the constraint c=t+p+−p− implies that if there is a penalisable excess of any component or property or feature then its value is p+ and if there is a penalisable shortage of any component or property or feature then its value is p−. These definitions must be made for every criterion in the objective function, that is, two for each component and property and feature (one per recipe and one per day). Any piecewise linear constraint or objective function can be modelled within integer programming.

Further components and properties and features can be added as new ingredients become available or new properties or features are investigated.

Several potential incompatibilities exist between streams; for instance, coffee flavour and juice ought not to be combined in the same drink. Constraints are added to ensure that incompatible streams are not included in servings together.

These constraints can be expressed linearly, since the quantity of each stream is bounded. The compatibilities of streams are given in Table 6.

In general if a linear constraint or set of constraints applies only under some condition that itself can be expressed as the violation of a second linear inequality or set of inequalities, this logical relationship can be expressed in the form of a mixed integer linear program.

A constraint ensures that the total mass of all streams sums to the desired amount. In one embodiment the desired amount is 400 g.

In one embodiment, a constraint is added to ensure that liquids form a sufficient proportion of the total drink.

In one embodiment, constraints limit total amounts of some streams in the serving.

In one embodiment, constraints ensure the inclusion of key streams. In one embodiment WPI is a key stream. In one embodiment MPC is a key stream.

The controller obtains limits on the availability of each stream in the machine and constrains the recipe to include no more of each stream than is available.

TABLE 6

| | \multicolumn{15}{c}{Compatibility} | | | | | | | | | | | | | | |
|---|---|---|---|---|---|---|---|---|---|---|---|---|---|---|---|
| | WPI | MPC | Juice | Omega | Folic acid | Sucralose solution | Probiotic | Vitamin E | Ca/Fe | Coffee Flavour | Chocolate flavour | Exotic flavour | Vitamins/ minerals | Hot water | Cold water |
| WPI | ✓ | | | | | | | | | | | | | | |
| MPC | ✓ | ✓ | | | | | | | | | | | | | |
| Juice | ✓ | ✓ | ✓ | | | | | | | | | | | | |
| Omega | ✓ | ✓ | ✓ | ✓ | | | | | | | | | | | |
| Folic acid | ✓ | ✓ | ✓ | ✓ | ✓ | | | | | | | | | | |
| Sucralose solution | ✓ | ✓ | ✓ | ✓ | ✓ | ✓ | | | | | | | | | |
| Probiotic | ✓ | ✓ | ✓ | ✓ | ✓ | ✓ | ✓ | | | | | | | | |
| Vitamin E | ✓ | ✓ | ✓ | ✓ | ✓ | ✓ | ✓ | ✓ | | | | | | | |
| Ca/Fe | ✓ | ✓ | ✓ | ✓ | ✓ | ✓ | ✓ | ✓ | ✓ | | | | | | |
| Coffee Flavour | ✓ | ✓ | X | ✓ | ✓ | ✓ | ✓ | ✓ | ✓ | ✓ | | | | | |
| Chocolate flavour | ✓ | ✓ | X | ✓ | ✓ | ✓ | ✓ | ✓ | ✓ | ✓ | ✓ | | | | |
| Exotic flavour | ✓ | ✓ | ✓ | ✓ | ✓ | ✓ | ✓ | ✓ | ✓ | ✓ | ✓ | ✓ | | | |
| Vitamins/ minerals | ✓ | ✓ | ✓ | ✓ | ✓ | ✓ | ✓ | ✓ | ✓ | ✓ | ✓ | ✓ | ✓ | | |
| cold water | ✓ | ✓ | ✓ | ✓ | ✓ | ✓ | ✓ | ✓ | ✓ | ✓ | ✓ | ✓ | ✓ | ✓ | |
| hot water | ✓ | ✓ | X | X | ✓ | ✓ | X | ✓ | ✓ | ✓ | ✓ | ✓ | ✓ | ✓ | ✓ |

Optimization Algorithm for Preparation of Beverage for User

Users' personal health profile may be obtained in a similar way to that described in Section 3 of the Boolean-Tree algorithm. Health profiles and drink preferences for five consumers are summarised in Table 2.

Based on this information, the recommended targets, minima and maxima per serve for various characteristics may be calculated for the five consumers. As an example, the nutritional requirements for Mike are shown in Table 7.

TABLE 7

Nutritional Targets and Weightings

| Characteristic | Target | Minimum | Maximum |
|---|---|---|---|
| Ca (mg) | 500 | 0 | 7000 |
| Vit C (mg) | 15 | 0 | 200 |
| Fe (mg) | 0 | 0 | 50 |
| Zinc (mg) | 3.8 | 0 | 50 |
| Mg (mg) | 100 | 0 | 2000 |
| Vit D (mg) | 0.0025 | 0 | 0.025 |
| Vit E (mg) | 5 | 0 | 20 |
| Thiamin (mg) | 0.38 | 0 | 2 |
| Riboflavin (mg) | 0.43 | 0 | 2 |
| Niacin (mg) | 4.9995 | 0 | 15 |
| Vit B6 (mg) | 0.5 | 0 | 2 |
| Folate (mg) | 0.1 | 0 | 1 |
| Vit B12 (mg) | 0.0015 | 0 | 0.09 |
| Protein (g) | 20 | 0 | 100 |
| Fibre (g) | 5 | 0 | 20 |
| Total CHO (g) | 12 | 0 | 60 |
| Pan. Acid (mg) | 2.5 | 0 | 10 |
| Omega 3 (mg) | 100 | 0 | 1000 |
| Probiotic (10^9 cfu) | 0 | 0 | 0 |
| Energy (kJ) | 620 | 0 | 4000 |

User preferences for flavour are also summarised in Table 2. In order to fulfil the requirements of a very sweet chocolate flavoured drink, the amount of chocolate in Mike's drink is set to 19.2 grams and the amount of Sucralose in the drink is set to 0.6 grams. The other drinks are similarly flavoured appropriately to the user preferences.

Penalty weightings and relative priorities for each user are also established according to their individual preferences and nutrition requirements, as described previously. Drinks can now be formulated using the optimisation algorithm. The composition of the drinks is shown in Table 8.

TABLE 8

Levels of Components and Features

| Composition | Sam | Mike | Matt | Carolyn | Sarah |
|---|---|---|---|---|---|
| Water (g) | 346.646 | 360.552 | 338.134 | 353.651 | 368.599 |
| Protein (g) | 22.5 | 18 | 27.5 | 18 | 12.527 |
| Fat (g) | 0.075 | 0.799 | 0.921 | 0.06 | 0.291 |
| Saturated fat (g) | 0.051 | 0.33 | 0.421 | 0.04 | 0.194 |
| Total CHO (g) | 27 | 15.629 | 27.001 | 22.505 | 14.248 |
| CHO, no fibre (g) | 19.273 | 10.062 | 20.572 | 15.701 | 9.248 |
| Fibre (g) | 7.727 | 5.067 | 5.929 | 6.804 | 5.001 |
| Complex CHO (g) | 0.058 | 0.032 | 0.058 | 0.107 | 2.475 |
| Sugar (g) | 19.215 | 9.278 | 20.513 | 13.048 | 6.475 |
| Lactose (g) | 0.198 | 9.863 | 14.349 | 2.705 | 6.78 |
| Ash (g) | 2.902 | 4.039 | 5.463 | 4.896 | 3.476 |
| Energy (kJ) | 831.801 | 593.011 | 947.439 | 679.319 | 459.226 |
| Energy-fat (kJ) | 2.807 | 30.115 | 34.703 | 2.247 | 10.963 |
| Ca (mg) | 267.158 | 708.287 | 998.757 | 553.916 | 550 |
| K (mg) | 1025.082 | 505.872 | 585.726 | 884.602 | 569.962 |
| P (mg) | 181.491 | 131.876 | 131.876 | 169.858 | 136.213 |
| Na (mg) | 54.576 | 2.304 | 0 | 43.676 | 0.74 |
| Cl (mg) | 5.074 | 0.112 | 0.112 | 4.081 | 0.111 |
| Fe (mg) | 0 | 0 | 0 | 4.95 | 0.088 |
| Mg (mg) | 109.025 | 101.334 | 103.697 | 105.163 | 106.36 |
| Zinc (mg) | 3.8 | 3.8 | 3.8 | 3.75 | 3.757 |
| Vit A (mg) | 0.086 | 0 | 0.028 | 0.058 | 0 |
| Vit C (mg) | 153.144 | 15.2 | 59.919 | 125.001 | 15.002 |
| Vit D (mg) | 0.003 | 0.003 | 0.003 | 0.003 | 0.003 |
| Vit E (mg) | 0 | 5 | 0 | 0 | 5 |
| Thiamin (mg) | 0.38 | 0.38 | 0.38 | 0.375 | 0.375 |
| Riboflavin (mg) | 0.431 | 0.431 | 0.431 | 0.425 | 0.425 |
| Niacin (mg) | 5.067 | 5.067 | 5.067 | 5.001 | 5.001 |
| Vit B6 (mg) | 0.507 | 0.507 | 0.507 | 0.5 | 0.5 |
| Folate (mg) | 0 | 0.1 | 0 | 0 | 0 |
| Vit B12 (mg) | 0.002 | 0.002 | 0.002 | 0.002 | 0.002 |
| Pan. Acid (mg) | 2.533 | 2.533 | 2.533 | 2.5 | 2.5 |
| Caffeine (mg) | 0 | 0 | 0 | 0 | 62.84 |
| Omega 3 (mg) | 0 | 100 | 100 | 0 | 0 |
| EPA + DHA (mg) | 0 | 80 | 80 | 0 | 0 |
| Probiotic (10^9 cfu) | 0 | 0 | 0 | 5 | 0 |

Table 9 shows the calculated prices of the drinks for the five consumers using both Boolean-Tree and Optimisation methods. The output of the Optimisation algorithm provides similar nutritional content in each case (see Table 5 for levels of components/features in the output of the Boolean-Tree algorithm), at a much cheaper price.

TABLE 9

Calculated Drink Price

| Algorithm | Sam | | Mike | | Matt | | Carolyn | | Sarah | |
|---|---|---|---|---|---|---|---|---|---|---|
| | Boolean-Tree | Optimisation | Boolean-Tree | Optimisation | Boolean-Tree | Optimisation | Boolean-Tree | Optimisation | Boolean-Tree | Optimisation |
| Price (cents) | 82.08 | 62.65 | 47.01 | 44.83 | 64.08 | 48.10 | 63.53 | 55.51 | 48.00 | 38.23 |

Solution Methods

The optimisation routine solves the optimisation problem thus formulated.

The optimisation is carried out using an optimisation algorithm or heuristic chosen in order to run as effectively as possible within a reasonable time frame. Since the capabilities of algorithms and the speed of computers are continually increasing, and the length of a reasonable time frame in which to run the optimisation algorithm or heuristic depends on the time between when the optimisation is used and the time at which the user is ready to receive the serving, and the complexity of the problem varies with the complexity of constraints and objective function criteria formulated in it, which may be changed from time to time, different embodiments of the invention may require different solution methods. The selection of possible solutions methods below is not intended to be limiting.

In one embodiment the objective function and all constraints are linear and the problem is thus a mixed integer linear program.

In one alternative the optimisation is carried out using mixed integer linear programming, as disclosed, for example, in Winston, W. L. (2004), Operations Research: Algorithms and Applications, $4^{th}$ Edition, Duxbury Press, incorporated herein by reference.

In one alternative the simplex method is used to solve linear relaxations of the mixed integer program, as disclosed, for example, in Winston, W. L. (2004), Operations Research: Algorithms and Applications, $4^{th}$ Edition, Duxbury Press, incorporated herein by reference.

In one alternative interior point methods are used to solve linear relaxations of the mixed integer program, as disclosed, for example, in Winston, W. L. (2004), Operations Research: Algorithms and Applications, $4^{th}$ Edition, Duxbury Press, incorporated herein by reference.

In one alternative the optimisation is carried out using threshold acceptance, as disclosed, for example, in Dueck, G. and Scheuer, T. (1990), Threshold accepting: a general purpose optimization algorithm appearing superior to simulated annealing, Journal of Computational Physics 104 pp86-92, incorporated herein by reference.

In one alternative the optimisation is carried out using multistart, as disclosed, for example in Rinnooy Kan, A. H. G. And Timmer, G. (1984), A stochastic approach to global optimization, in Numerical Optimization (P. Boggs, R. Byrd and R. B. Schnabel, Eds.), SIAM, Philadelphia, incorporated herein by reference.

In one alternative the optimisation is carried out using simulated annealing, as disclosed, for example, in Kirkpatrick, S., Gelatt, C. D. Jr. And Vecchi, M. P. (1983), Optimization by simulated annealing, Science 220 pp671-680, incorporated herein by reference.

In one alternative the optimisation is carried out using the great deluge, as disclosed, for example, in Dueck, G. (1993), New optimization heuristics: the great deluge algorithm and the record-to-record travel, Journal of Computational Physics 104 pp86-92, incorporated herein by reference.

In one alternative the optimisation is carried out using tabu search, as disclosed, for example, in Glover, F. and Laguna, M (1997), Tabu Search, Kluwer Academic Publishers, Boston, incorporated herein by reference.

In one alternative the optimisation is carried out using controlled random search, as disclosed, for example, in Price, W. L. (1978), A controlled random search procedure for global optimization, in Towards Global Optimization 2 (L. C. W. Dixon and G. P. Szegö, Eds.), North-Holland, Amsterdam, incorporated herein by reference.

In one alternative the optimisation is carried out using genetic algorithms, as disclosed, for example, in Holland, J. H. (1975), Adaptation in natural and artificial systems, The University of Michigan Press, Ann Arbor, incorporated herein by reference.

In one alternative the optimisation is carried out using neural networks, as disclosed, for example, in Hopfield, J. J. and Tank, D. W. (1985), "Neural" computation of decisions in optimization processes, Biological Cybernetics 52 pp141-152, incorporated herein by reference.

In one alternative the optimisation is carried out using evolutionary algorithms, as disclosed, for example, in Rachenberg, I. (1973), Evolution strategie: Optimierung technischer systeme nach prinzipien der biologischen evolution, Frommann-Holzboog, Stuttgart, incorporated herein by reference.

In one alternative the optimisation is carried out using the Nelder-Mead algorithm, as disclosed, for example, in Nelder, J. A. and Mead, R. (1965), A simplex method for function minimization, The Computer Journal 7 pp308-313, incorporated herein by reference.

In one alternative the optimisation is carried out using particle swarms, as disclosed, for example, in Eberhart, R. C. and Kennedy, J. (1995), A new optimizer using particle swarm theory, Proceedings of the Sixth International Symposium on Micromachine and Human Science, Nagoya, Japan, pp 39-43, incorporated herein by reference.

In one alternative the optimisation is carried out using simulated ant colonies, as disclosed, for example, in Colorni A., Dorigo, M. and Maniezzo, V. (1992) Distributed Optimization by Ant Colonies, Proceedings of the First European Conference on Artificial Life, Paris, France (F. Varela and P. Bourgine, Eds.), Elsevier Publishing, pp134-142, incorporated herein by reference.

In one alternative the optimisation is carried out using gradient methods, as disclosed, for example, in Golub, G. and O'Leary, D. (1989), Some History of the Conjugate Gradient and Lanczos Methods, SIAM Rev 31, p50-102, incorporated herein by reference.

Although the present invention has been described in detail with reference to examples and particular embodiments above, it is understood that various modifications can be made without departing from the spirit of the invention. Accordingly, the invention is limited only by the following claims. All cited patents, patent applications and publications referred to in this application are herein incorporated by reference in their entirety.

REFERENCES

Winston, W. L. (2004), Operations Research: Algorithms and Applications, $4^{th}$ Edition, Duxbury Press.

Dueck, G. and Scheuer, T. (1990), Threshold accepting: a general purpose optimization algorithm appearing superior to simulated annealing, Journal of Computational Physics 104 pp86-92.

Rinnooy Kan, A. H. G. And Timmer, G. (1984), A stochastic approach to global optimization, in Numerical Optimization (P. Boggs, R. Byrd and R. B. Schnabel, Eds.), SIAM, Philadelphia.

Kirkpatrick, S., Gelatt, C. D. Jr. And Vecchi, M. P. (1983), Optimization by simulated annealing, Science 220 pp671-680.

Dueck, G. (1993), New optimization heuristics: the great deluge algorithm and the record-to-record travel, Journal of Computational Physics 104 pp86-92.

Glover, F. and Laguna, M (1997), Tabu Search, Kluwer Academic Publishers, Boston.

Price, W. L. (1978), A controlled random search procedure for global optimization, in Towards Global Optimization 2 (L. C. W. Dixon and G. P. Szegö, Eds.), North-Holland, Amsterdam.

Holland, J. H. (1975), Adaptation in natural and artificial systems, The University of Michigan Press, Ann Arbor.

Hopfield, J. J. and Tank, D. W. (1985), "Neural" computation of decisions in optimization processes, Biological Cybernetics 52 pp141-152.

Rechenberg, I. (1973), Evolution strategie: Optimierung technischer systeme nach prinzipien der biologischen evolution, Frommann-Holzboog, Stuttgart.

Nelder, J. A. and Mead, R. (1965), A simplex method for function minimization, The Computer Journal 7 pp308-313.

Eberhart, R. C. and Kennedy, J. (1995), A new optimizer using particle swarm theory, Proceedings of the Sixth International Symposium on Micromachine and Human Science, Nagoya, Japan, pp 39-43.

Colomi A., Dorigo, M. and Maniezzo, V. (1992) Distributed Optimization by Ant Colonies, Proceedings of the First European Conference on Artificial Life, Paris, France (F. Varela and P. Bourgine, Eds.), Elsevier Publishing, pp134-142.

Golub, G. and O'Leary, D. (1989), Some History of the Conjugate Gradient and Lanczos Methods, SIAM Rev 31, p50-102.

What is claimed is:

1. A system for dispensing a customized nutritional serving which comprises:
    an ingredient storage module;
    an ingredient processing module;
    a serving dispenser;
    a customer interface; and
    a controller operatively linked to the customer interface and programmed to control the storage module, the processing module and the serving dispenser;
    the controller having stored in its memory an inventory of ingredients in the storage module, their compositions and their properties, and customer profile data;
    the controller being programmed to operate in the following manner:
    when a customer selects a customized serving through the customer interface, the controller:
    a) looks up the information stored in its memory, formulates a serving which best matches the customized serving selected by the customer within predetermined constraints set by its programming and presents a selected serving to the customer for confirmation or modification;
    b) if the customer modifies the selection, repeats step a) on the modified selection, and presents the resulting selected serving to the customer for confirmation or modification; and
    c) when the customer has confirmed a serving issues instructions to the ingredient storage and processing modules and the serving dispenser to prepare and dispense the serving.

2. The system as claimed in claim 1, wherein the ingredient processing module and the serving dispenser are integral with one another.

3. The system as claimed in claim 1, wherein the serving dispenser is at least partly operated by a customer or by an operator.

4. The system as claimed in claim 1, wherein the predetermined constraints in the programming of the controller include but are not limited to one or more of the following:
    limitations on physical properties of ingredients,
    the compatibility of ingredients with one another,
    limitations on certain ingredients by health status,
    requirements of certain ingredients by health status,
    availability of ingredients in the inventory, and cost.

5. The system as claimed in claim 1, wherein the controller is programmed so that as if a repeat customer is identified through the customer interface, the customer is presented with a selected serving based on a previous selection of that customer, and if the customer confirms the selection the controller skips directly to step c), while if the customer selects a different serving the controller begins at step a).

6. The system as claimed in claim 1, wherein in carrying out steps a) and b) the controller:
    uses the customer profile data to generate nutritional requirements and targets for the customer and consults the inventory of ingredients to generate limits on the inclusion levels of each ingredient, and
    selects ingredients to formulate a serving optimised to meet nutritional requirements within the constraints of available ingredients.

7. The system as claimed in claim 6, wherein the controller selects ingredients to formulate a serving optimised to meet nutritional requirements within the constraints of other requirements.

8. The system as claimed in claim 7, wherein the other requirements include requirements that certain ingredients are not included together at incompatible levels and that the serving comprises sufficient but not excessive liquid ingredients in a way that departs as little as possible from nutritional targets, that matches as closely as possible the customer's preferred flavour choices, and that is as inexpensive as possible.

9. The system as claimed in claim 1, wherein in the steps a) and b) the selected serving presented to the customer is determined through the use of a boolean-tree algorithm.

10. The system as claimed in claim 6, wherein in the steps a) and b) the selected serving presented to the customer is determined through the use of mixed integer linear programming.

11. A system as claimed in claim 1, wherein the ingredient storage module comprises a plurality of storage compartments.

12. A system as claimed in claim 1, wherein the ingredients storage module contains a dosing means for dosing predetermined amounts of ingredients stored in compartments into a serving.

13. A system as claimed in any claim 1, wherein there is provided ingredient advancing means for moving ingredients from the ingredients storage module to the ingredient processing module.

14. A system as claimed in claim 1, wherein the controller is operatively linked to one or more servers each having stored in its memory at least some of the inventory of ingredients in the storage module and possible servings available therefrom, nutritional and health data relating to ingredients in the storage module and possible servings therefrom, and at least some of the customer profile data.

15. A system as claimed in claim 14, wherein the controller and/or server is operatively linked to an external database.

16. A system as claimed in claim 15, wherein the external database contains information on health and nutrition.

17. A system as claimed in claim 15, wherein the external database contains health information of a customer.

18. A system as claimed in claim 1, wherein the customer profile data includes health status, records of recent purchases and preferences.

19. A system as claimed in claim 1, wherein the customer interface is a touch panel or keyboard integral with the dispensing system.

20. A system as claimed in claim 1, wherein the customer interface is a cell phone operable from a location remote from the dispensing system.

21. A system as claimed in claim 1, wherein the customer interface is a customer computer operatively linked through to the internet to the system.

22. A system as claimed in claim 1, wherein the customer interface is a card reader which reads information digitally or magnetically stored on a card presented by a customer.

23. A system as claimed in claim 1, wherein the controller is operatively linked to a billing function.

24. A system as claimed in claim 23, wherein the billing function is operatively linked to an electronic crediting/debiting system.

25. A system as claimed in claim 23, wherein the billing function is actuable by the insertion of coins, banknotes, prepaid electronic cards or the like.

26. A network of systems as claimed in claim 1, operatively linked to one or more servers.

* * * * *